US009821043B2

(12) United States Patent
Michaelis et al.

(10) Patent No.: US 9,821,043 B2
(45) Date of Patent: Nov. 21, 2017

(54) ANTI-HER2 VACCINE BASED UPON AAV DERIVED MULTIMERIC STRUCTURES

(75) Inventors: Uwe Michaelis, Weilheim (DE); Erika Jensen-Jarolim, Vienna (AT); Christoph Rehfuess, München (DE); Margit Weghofer, Vienna (AT)

(73) Assignee: Medigene AG, Planegg-Martinsried (DE)

( * ) Notice: Subject to any disclaimer, the term of this patent is extended or adjusted under 35 U.S.C. 154(b) by 401 days.

(21) Appl. No.: 14/344,783

(22) PCT Filed: Sep. 14, 2012

(86) PCT No.: PCT/EP2012/068110
§ 371 (c)(1),
(2), (4) Date: Mar. 10, 2015

(87) PCT Pub. No.: WO2013/037961
PCT Pub. Date: Mar. 21, 2013

(65) Prior Publication Data
US 2015/0238585 A1    Aug. 27, 2015

Related U.S. Application Data

(60) Provisional application No. 61/535,124, filed on Sep. 15, 2011.

(51) Int. Cl.
| | |
|---|---|
| *A61K 39/23* | (2006.01) |
| *A61K 39/385* | (2006.01) |
| *C12N 7/00* | (2006.01) |
| *C12P 21/00* | (2006.01) |
| *C07K 14/71* | (2006.01) |
| *C07K 14/435* | (2006.01) |
| *C07K 14/015* | (2006.01) |
| *A61K 39/00* | (2006.01) |
| *C07K 14/005* | (2006.01) |
| *A61K 39/39* | (2006.01) |

(52) U.S. Cl.
CPC ......... *A61K 39/0011* (2013.01); *A61K 39/39* (2013.01); *C07K 14/005* (2013.01); *C07K 14/71* (2013.01); *C12N 7/00* (2013.01); *C12P 21/00* (2013.01); *A61K 2039/5258* (2013.01); *A61K 2039/54* (2013.01); *A61K 2039/543* (2013.01); *A61K 2039/545* (2013.01); *A61K 2039/55505* (2013.01); *A61K 2039/55561* (2013.01); *A61K 2039/55572* (2013.01); *A61K 2039/575* (2013.01); *A61K 2039/6075* (2013.01); *A61K 2039/645* (2013.01); *C07K 2319/00* (2013.01); *C07K 2319/735* (2013.01); *C12N 2750/14022* (2013.01); *C12N 2750/14023* (2013.01); *C12N 2750/14122* (2013.01); *C12N 2750/14123* (2013.01); *Y10T 428/2984* (2015.01)

(58) Field of Classification Search
None
See application file for complete search history.

(56) References Cited

U.S. PATENT DOCUMENTS 6,719,978 B2 *  4/2004  Schiller ............ A61K 47/48776
424/133.1
6,846,665 B1    1/2005  Hörer et al.

FOREIGN PATENT DOCUMENTS

| WO | 01/05990 A1 | | 1/2001 |
|---|---|---|---|
| WO | 01/05991 A1 | | 1/2001 |
| WO | WO01/41787 | * | 6/2001 |
| WO | 03/054197 A2 | | 7/2003 |
| WO | 2008/145400 A2 | | 12/2008 |
| WO | 2008/145401 A2 | | 12/2008 |
| WO | 2008145400 A2 | | 12/2008 |
| WO | 2008145401 A2 | | 12/2008 |
| WO | 2010/099950 A2 | | 9/2010 |

OTHER PUBLICATIONS

Riemer et al (Molecular Immunology, 2006, vol. 42, pp. 1121-1124).*
International Search Report issued on Mar. 12, 2012 by the European Patent Office as the International Searching Authority in International Patent Application No. PCT/EP2012/068110.
Bernhard et al., "Vaccination against the HER-2/neuoncogenic protein", Endocrine-Related Cancer, 2002, vol. 9, pp. 33-44.
Florence Corpet, "Multiple sequence alignment with hierarchical clustering", Nucleic Acids Research, 1988, vol. 16, pp. 10881-10890.
Dakappagari et al., "Prevention of Mammary Tumors with a Chimeric HER-2 B-cell Epitope Peptide Vaccine", Cancer Research, 2000, vol. 60, pp. 3782-3789.
Dakappagari et al., "A Chimeric Multi-Human Epidermal Growth Factor Receptor-2 B Cell Epitope Peptide Vaccine Mediates Superior Antitumor Responses". The Journal of Immunology, 2003, vol. 170, pp. 4242-4253.
Dakappagari et al., "Conformational HER-2/neu B-cell Epitope Peptide Vaccine Designed to Incorporate Two Native Disulfide Bonds Enhances Tumor Cell Binding and Antitumor Activities", The Journal of Biological Chemistry, 2005, vol. 280, pp. 54-63.
Disis et al., "Peptide-Based, but Not Whole Protein, Vaccines Elicit Immunity to HER-2/neu, an Oncogenic Self-Protein". The Journal of Immunology, 1996, vol. 156, pp. 3151-3158.
Disis et al., "Generation of Immunity to the HER-2/neu Oncogenic Protein in Patients with Breast and Ovarian Cancer Using a Peptide-based Vaccine". Clinical Cancer Research, 1999, vol. 5, pp. 1289-1297.

(Continued)

*Primary Examiner* — Karen Canella
(74) *Attorney, Agent, or Firm* — Lee & Hayes, PLLC

(57) ABSTRACT

The present invention relates to parvovirus mutated structural proteins comprising insertions of mimotopes of a HER2, compositions, multimeric structures, medicaments and vaccines comprising the same, nucleic acids, expression cassettes, constructs, vectors and cells comprising the nucleic acids, methods of preparing the structural proteins and methods of inducing a B-cell response or of treating a HER2-related disease.

35 Claims, 5 Drawing Sheets

(56) References Cited

OTHER PUBLICATIONS

Figure 1:
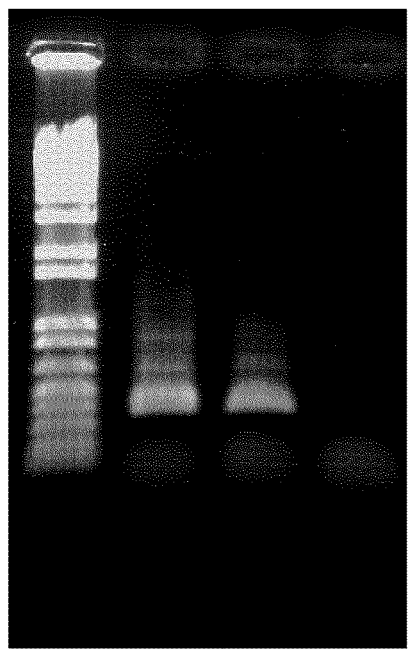

Disis et al., "Generation of T-Cell Immunity to the HER-2/neu Protein After Active Immunization with HER-2/neu Peptide-Based Vaccines", Journal of Clinical Oncology, 2002. vol. 20, pp. 2624-2632.

Disis et al., "Concurrent Trastuzumab and HER2/neu-Specific Vaccination in Patients with Metastatic Breast Cancer". Journal of Clinical Oncology, 2009, vol. 27, pp. 4685-4692.

Ercolini et al., "Identification and Characterization of the Immunodominant Rat HER-2/neu MHC Class I Epitope Presented by Spontaneous Mammary Tumors from HER-2/neu-Transgenic Mice". The Journal of Immunology, 2003, vol. 170, pp. 4273-4280.

Esserman et al., "Vaccination with the extracellular domain of p185neu prevents mammary tumor development in neu transgenic mice" Cancer Immunol Immunother, 1999, vol. 47, pp. 337-342.

Fields, "Virology", Fourth Edition, vol. 2, Chapter 69, Lippincott Williams Wilkins, Philadelphia.

Friedländer et al., "ErbB-directed immunotherapy: Antibodies in current practice and promising new agents". Immunology Letters, 2008, vol. 116, pp. 126-140.

Grimm et al., "Titration of AAV-2 particles via a novel capsid ELISA: packaging of genomes can limit production of recombinant AAV-2", Gene Therapy, 1999, vol. 6, pp. 1322-1330.

Harries and Smith, "The development and clinical use of trastuzumab (Herceptin)" Endocrine-Related Cancer, 2002, vol. 9, pp. 75-85.

Heilbronn et al., "The Adeno-Associated Virus rep Gene Suppresses Herpes Simplex Virus-Induced DNA Amplification" Journal of Virology, 1990, vol. 64, pp. 3012-3018.

Hynes and Stern, "The biology of erbB-2/neu/HER-2 and its role in cancer", Biochimica et Biophysica Acta, 1994, vol. 1198, pp. 165-184.

Jasinska et al., "Inhibition of tumor cell growth by antibodies induced after vaccination with peptides derived from the extracellular domain of HER-2/neu", International Journal of Cancer, 2003, vol. 107, pp. 976-983.

Ladjemi et al., "Anti-HER2 vaccines new prospects for breast cancer therapy". Cancer Immunol Immunother, 2010, vol. 59, pp. 1295-1312.

Müller et al., "Immunological Approaches in the Treatment of Metastasized Breast Cancer", Breast Care, 2009, vol. 4, pp. 359-366.

Nahta and Esteva, "Herceptin: mechanisms of action and resistance". Cancer Letters. 2006, vol. 232, pp. 123-138.

Partidos, C. D., "Peptide mimotopes as candidate vaccines". Current Opinion in Molecular Therapeutics, 2000, vol. 2, pp. 74-79.

Peoples et al., "Combined Clinical Trial Results of a HER2/neu (E75) Vaccine for the Prevention of Recurrence in High-Risk Breast Cancer Patients: U.S. Military Cancer Institute Clinical Trials Group Study I-01 and I-02", Clinical Cancer Research, 2008, vol. 14, pp. 797-803.

Reilly et al., "HER-2/neu Is a Tumor Rejection Target in Tolerized HER-2/neu Transgenic Mice", Cancer Research, 2000, vol. 60, pp. 3569-3576.

Riemer and Jensen-Jarolim, "Mimotope vaccines: Epitope mimics induce anti-cancer antibodies", Immunology Letters, 2007, vol. 113, pp. 1-5.

Riemer et al., "Generation of Peptide Mimics of the Epitope Recognized by Trastuzumab on the Oncogenic Protein Her-2/neu", The Journal of Immunology, 2004, vol. 173, pp. 394-401.

Ross et al., "The HER-2 Receptor and Breast Cancer: Ten Years of Targeted Anti-HER-2 Therapy and Personalized Medicine", The Oncologist, 2009, vol. 14, pp. 320-368.

Scholl et al., "Targeting HER2 in other tumor types", Annals of Oncology, 2001, vol. 12, pp. S81-S87.

Slamon et al., "Use of chemotherapy plus a monoclonal antibody against HER2 for metastatic breast cancer that overexpresses HER2", The New England Journal of Medicine, 2001, vol. 344, pp. 783-792.

Sonntag et al., "A viral assembly factor promotes AAV2 capsid formation in the nucleolus", Proceedings of the National Academy of Sciences, 2010, vol. 107, pp. 10220-10225.

Vogel et al., "Efficacy and Safety of Trastuzumab as a Single Agent in First-Line Treatment of HER2-Overexpressing Metastatic Breast Cancer", Journal of Clinical Ontology, 2002, vol. 20, pp. 719-726.

Warrington, et al., "Adeno-Associated Virus Type 2 VP2 Capsid Protein is Nonessential and Can Tolerate Large Peptide Insertions at its N Terminus", Journal of Virology, 2004, vol. 78, pp. 6595-6609.

Laird and Greenstein, "Parvovirus", 2000. URL: [http://web.stanford.edu/group/virus/parvo/2000/parvovirus.html].

* cited by examiner

SEQUENCE LISTING

```
<160> NUMBER OF SEQ ID NOS: 168

<210> SEQ ID NO 1
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 1

Arg Leu Val Pro Val Gly Leu Glu Arg Gly Thr Val Asp Trp Val
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 2

Thr Arg Trp Gln Lys Gly Leu Ala Leu Gly Ser Gly Asp Met Ala
1               5                   10                  15
```

-continued

<210> SEQ ID NO 3
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 3

Arg Thr Trp Gln Ser Gly Met Ala Asp Gly Glu Glu Ile Gly Arg
1 5 10 15

<210> SEQ ID NO 4
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 4

Gln Val Ser His Trp Val Ser Gly Leu Ala Glu Gly Ser Phe Gly
1 5 10 15

<210> SEQ ID NO 5
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 5

Ser Ser Trp Ala Ala Gly Thr Ala Ala Gly Asp Phe Lys Gly Tyr
1 5 10 15

<210> SEQ ID NO 6
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 6

Leu Ser His Thr Ser Gly Arg Val Glu Gly Ser Val Ser Leu Leu
1 5 10 15

<210> SEQ ID NO 7
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 7

Ser Leu Trp Leu Leu Gly Arg Ala Asp Gly Val Ser Ser Gly His
1 5 10 15

<210> SEQ ID NO 8
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 8

Gln Gly Arg Ala Lys Asn Leu Pro Asn Cys Gly Ser Gly Gln Arg
1 5 10 15

-continued

<210> SEQ ID NO 9
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 9

Arg Ser Phe Glu Lys Phe Gly Gly Met Lys Glu Arg Leu His Cys
1 5 10 15

<210> SEQ ID NO 10
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 10

Ala Val Glu Pro Cys Ile Thr Ala His Lys Ser Tyr Met Arg Val
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 11

Ser Thr Leu Trp His Arg Gly Leu Ala Ala Gly Asp Val Ser Arg
1 5 10 15

<210> SEQ ID NO 12
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 12

Ser Glu Ser Gly Val Phe Val Leu Gln Ser Cys Ala Trp Glu Tyr
1 5 10 15

<210> SEQ ID NO 13
<211> LENGTH: 15
<212> TYPE: PRT
<213> ORGANISM: Artificial sequence
<220> FEATURE:
<223> OTHER INFORMATION: peptide binding to trastuzumab

<400> SEQUENCE: 13

Trp Gly Asn Cys Pro Leu Ser Ser Gly Gly Pro Lys Thr Phe Arg
1 5 10 15

<210> SEQ ID NO 14
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 14

Trp Val Gly Ser Arg Ser Met Trp Ala Glu Cys Gly Leu Asp Glu
1 5 10 15

<210> SEQ ID NO 15

```
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 15

Leu Asp Ser Thr Ser Leu Ala Gly Gly Pro Tyr Glu Ala Ile Glu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 16

Leu Ser Arg Cys Gly Lys Pro Met Asp Val Glu Ala Ala Leu Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 17

Phe Pro Lys Ser Gln Val Ser Arg Gly Glu Met Arg Leu Gly Gly
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: peptide binding to trastuzumab

<400> SEQUENCE: 18

Phe Phe Ser Gly Arg Trp Ser Glu Gly Thr Ala Leu Gly Ser Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 19

His Val Val Met Asn Trp Met Arg Glu Glu Phe Val Glu Glu Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 20

Gly Val Ala Trp Ser Ser Gly Gln Ala His Gly Ser Arg Thr Glu
1               5                   10                  15

<210> SEQ ID NO 21
<211> LENGTH: 15
```

-continued

<212> TYPE: PRT
<213> ORGANISM: Artificial Sequence
<220> FEATURE:
<223> OTHER INFORMATION: peptide binding to trastuzumab

<400> SEQUENCE: 21

Trp Asp Ser Gly Asp Ala Val Gly Asn Glu Val Leu Leu Val Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 22

Trp Lys Met Gly Thr Ala Gln Gly Ser Gly Gln Asp Gly Glu Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 23

Gly Trp Asn Ser Gly Lys Val Asp Gly Gly Ala Gly Arg Ser Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 24

Leu Val Gly Val Trp Pro Val Met Val Glu Thr Val Tyr Glu Thr
1               5                   10 15

<210> SEQ ID NO 25
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 25

Gln Trp Leu Glu Gly Leu Ala Glu Gly Met Val His Thr Leu Gly
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 26

Asp Pro Tyr Glu Ser Ser Arg Ser Thr Leu Leu Arg Ala Ala Arg
1 5 10 15

<210> SEQ ID NO 27
<211> LENGTH: 15
<212> TYPE: PRT

-continued

<213> ORGANISM: Artificial Sequence
<220> FEATURE:
<223> OTHER INFORMATION: peptide binding to trastuzumab

<400> SEQUENCE: 27

Gly Asp Glu Glu Met Trp Pro Ile Val Arg Glu Leu Gln Ser Leu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 28

Leu Lys Trp Tyr Ser Gly Glu Leu Glu Gly Ser Lys Glu Leu Leu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 29

Asn Pro Gly Thr Trp Glu Arg Gly Val Ala Ala Gly Asp Ile Glu
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 30

Gln Thr Lys Trp Pro Ile Ala Thr Glu Val Trp Arg Glu Thr Val
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 31

Val Gly Ala Ala Ala Gln Trp Pro Glu Val Arg Glu Tyr Leu Met
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 32

Tyr Phe Ser Gly Lys Ala Glu Gly Arg Glu Ala Pro Ser Trp Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 33

Cys Asp Val Gln Leu Ala Ser Ala Lys Lys Arg Tyr Leu Gly Val
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 34

Cys Met Gly Val Val Lys Ala Trp Asp Ser Ile Arg Leu Val Glu
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 35

Asp Val Gly Gln Gly Arg Arg Lys Ser Leu Asn Leu Glu Cys Phe
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 36

Asp Val Thr Trp Arg His Lys His Ile Val Thr Lys Gly Gly Leu
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 37

Gly Gly Tyr Glu Val Arg Lys His Phe Gln Ser Arg Glu Val Val
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 38

Lys Asn Cys Asp Arg Leu Ser Trp Ser Gly Ala Arg Asn Leu Ser
1 5 10 15

<210> SEQ ID NO 39
<211> LENGTH: 15
<212> TYPE: PRT
<213> ORGANISM: Artificial Sequence
<220> FEATURE:

-continued

<223> OTHER INFORMATION: peptide binding to trastuzumab

<400> SEQUENCE: 39

Leu Val Glu His Trp Ser Arg Ser Lys Lys Ser Ser Phe Glu Phe
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 40

Leu Val Ser Val Gln Lys Lys Trp Glu Arg Lys Ala Glu Ser Met
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 41

Met Phe Leu Ser Asp Lys Tyr Ser Arg Glu Pro His Lys Gly Lys
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 42

Arg Arg Thr Leu Cys Gly Thr Gly Ser Glu Met Val Leu Phe Lys
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 43

Ser Val Arg Leu Ser Ser Ala Gln Gly Cys Ile Asn Met Val Val
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 44

Ser Trp Ala Ser Gly Met Ala Val Gly Ser Val Ser Phe Glu Glu
1 5 10 15

<210> SEQ ID NO 45
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 45

Val Thr Gly Asn Cys Lys Gly Ser Arg Gln Gln His Val Leu Gly
1 5 10 15

<210> SEQ ID NO 46
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 46

Trp Trp Ala His Gly Glu Asp Ile Thr Gly His Ser Leu Cys Leu
1 5 10 15

<210> SEQ ID NO 47
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 47

Ala Ser Gln Gly Ser Trp Lys Leu Gly Thr Ala Arg Gly Ser Gly
1 5 10 15

<210> SEQ ID NO 48
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 48

Met Gln Leu Ile Cys Arg Thr Ser Leu Arg Glu Glu Arg Ile Ile
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 49

Arg Phe Ser Cys Ala Val Gly Lys Glu Cys Ser His Lys Gln Cys
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 50

Arg Ser Asn Asp Val Leu Gly Cys Lys Leu Arg Val Val Gly Cys
1 5 10 15

<210> SEQ ID NO 51
<211> LENGTH: 9
<212> TYPE: PRT
<213> ORGANISM: Artificial Sequence
<220> FEATURE:
<223> OTHER INFORMATION: peptide binding to trastuzumab
<220> FEATURE:

<221> NAME/KEY: MISC_FEATURE
<222> LOCATION: (2)..(3)
<223> OTHER INFORMATION: X = any amino acid
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (7)..(7)
<223> OTHER INFORMATION: X = any amino acid

<400> SEQUENCE: 51

Trp Xaa Xaa Gly Xaa Ala Xaa Gly Ser
1               5

<210> SEQ ID NO 52
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 52

Trp Ala Phe Gly Leu Ala Leu Gly Ser Leu Glu Thr Ile Asp Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 53

Trp Gly Glu Pro Tyr Ser Gly Lys Gly Ser His Gly Lys Ile Gly
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 54

Ala Ser Ala Trp Leu Leu Gly Asn Val Glu Gly Ser Glu Ile Arg
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 55

Cys Gln Trp Arg Ala Gly Thr Ala Val Gly Ser Ser Val Gly Asn
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 56

His Glu Val Leu Trp Gly Glu Met Asp Ala Pro Trp Val Val Pro
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 57

Ile Ala Ser Gly Trp Ser Val Gly Trp Ala Asp Gly Asp Asp Ser
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 58

Pro Tyr Glu Glu Leu Val Ala Thr Arg Ser Arg Ala Gly Gly Met
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 59

Ser Cys Leu Ala Arg Val His Cys Asp Met Pro Arg Glu Trp Glu
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 60

Val Ala Thr Lys Gly Val Thr Leu Trp Glu Thr Gly Leu Ala Glu
1 5 10 15

<210> SEQ ID NO 61
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 61

Val Thr Leu Met Lys Ile Ser Lys Trp Asp Ala Gly Leu Ala Glu
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 62

Trp Met Ser Gly Gln Ser Asp Gly Ser Ser Gly Gly Gly Pro Lys

-continued 1 5 10 15

<210> SEQ ID NO 63
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 63

Arg Glu Ala Gly Gln Trp Ala Arg Gly Leu Ala Val Gly Ser Cys
1 5 10 15

<210> SEQ ID NO 64
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 64

Tyr Val Ile Gly Pro Tyr Glu Arg Glu Cys Glu Leu Gly Met Gly
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: peptide binding to trastuzumab

<400> SEQUENCE: 65

Trp Lys Met Gly Met Ala Gln Gly Ser Gly Gln Asp Gly Glu Tyr
1 5 10 15

<210> SEQ ID NO 66
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Trp, His, Tyr or Val
<220> FEATURE:
<221> NAME/KEY: MISC_FEATURE
<222> LOCATION: (2)..(3)
<223> OTHER INFORMATION: X = any amino acid
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Ala, Leu, Val, Cys or Glu
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (9)..(9)
<223> OTHER INFORMATION: X = Ser, Met, Asp, Glu, Val, Asn, Gly, Arg or
Thr

<400> SEQUENCE: 66

Xaa Xaa Xaa Gly Xaa Xaa Xaa Gly Xaa
1 5

```
<210> SEQ ID NO 67
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(3)
<223> OTHER INFORMATION: X = any amino acid
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Ala, Val or Leu
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (9)..(9)
<223> OTHER INFORMATION: X = Ser, Thr, Me, tAsp or Glu

<400> SEQUENCE: 67

Trp Xaa Xaa Gly Xaa Xaa Xaa Gly Xaa
1               5

<210> SEQ ID NO 68
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ser, Thr, Lys, Arg, Met, Leu, Ala or Val
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Ala or Val
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (9)..(9)
<223> OTHER INFORMATION: X = Ser, Met or Asp

<400> SEQUENCE: 68

Trp Xaa Xaa Gly Xaa Xaa Xaa Gly Xaa
1               5

<210> SEQ ID NO 69
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
```

```
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Lys, Arg, Glu, Ser, Thr or Phe
<220> FEATURE:
<221> NAME/KEY: MISC_FEATURE
<222> LOCATION: (5)..(5)
<223> OTHER INFORMATION: X = Leu, Met, Thr or Val
<220> FEATURE:
<221> NAME/KEY: MISC_FEATURE
<222> LOCATION: (7)..(7)
<223> OTHER INFORMATION: X = Ala, Val, Leu, Glu or Asp
<220> FEATURE:
<221> NAME/KEY: MISC_FEATURE
<222> LOCATION: (9)..(9)
<223> OTHER INFORMATION: X = Ser, Thr, Asp, Glu or Met

<400> SEQUENCE: 69

Trp Xaa Xaa Gly Xaa Ala Xaa Gly Xaa
1               5

<210> SEQ ID NO 70
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Ser, Thr or Gly
<220> FEATURE:
<221> NAME/KEY: MISC_FEATURE
<222> LOCATION: (2)..(2)
<223> OTHER INFORMATION: X = Ser, Thr, Arg, Gln, His or Leu
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = Lys, Arg, Ser, Glu or Phe
<220> FEATURE:
<221> NAME/KEY: MISC_FEATURE
<222> LOCATION: (7)..(7)
<223> OTHER INFORMATION: X = Leu, Met, Thr or Val
<220> FEATURE:
<221> NAME/KEY: MISC_FEATURE
<222> LOCATION: (9)..(9)
<223> OTHER INFORMATION: X = Ala, Val, Leu or Glu
<220> FEATURE:
<221> NAME/KEY: MISC_FEATURE
<222> LOCATION: (11)..(11)
<223> OTHER INFORMATION: X = Ser, Asp or Met
<220> FEATURE:
<221> NAME/KEY: MISC_FEATURE
<222> LOCATION: (12)..(12)
<223> OTHER INFORMATION: X = Gly, Val, Leu, Ile, Ser, Cys or Phe

<400> SEQUENCE: 70

Xaa Xaa Trp Xaa Xaa Gly Xaa Ala Xaa Gly Xaa Xaa
1               5                   10

<210> SEQ ID NO 71
<211> LENGTH: 10
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
```

```
<223> OTHER INFORMATION: X = Ser, Thr, Leu or Gln
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (4)..(4)
<223> OTHER INFORMATION: X = Met, Ala, Leu or Val
<220> FEATURE:
<221> NAME/KEY: MISC_FEATURE
<222> LOCATION: (6)..(6)
<223> OTHER INFORMATION: X = Thr, Ala, Ser or Met
<220> FEATURE:
<221> NAME/KEY: MISC_FEATURE
<222> LOCATION: (8)..(8)
<223> OTHER INFORMATION: X = Gln, Ala, Val, His, Lys or Arg
<220> FEATURE:
<221> NAME/KEY: MISC_FEATURE
<222> LOCATION: (10)..(10)
<223> OTHER INFORMATION: X = Ser, Thr, Asp or Glu

<400> SEQUENCE: 71

Xaa Trp Xaa Xaa Gly Xaa Ala Xaa Gly Xaa
1               5                   10

<210> SEQ ID NO 72
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Ser, Thr or Gly
<220> FEATURE:
<221> NAME/KEY: MISC_FEATURE
<222> LOCATION: (2)..(2)
<223> OTHER INFORMATION: X = Ser, Thr or Gln
<220> FEATURE:
<221> NAME/KEY: MISC_FEATURE
<222> LOCATION: (4)..(4)
<223> OTHER INFORMATION: X = Lys, Arg or Ala
<220> FEATURE:
<221> NAME/KEY: MISC_FEATURE
<222> LOCATION: (5)..(5)
<223> OTHER INFORMATION: X = Met, Ala or Leu
<220> FEATURE:
<221> NAME/KEY: MISC_FEATURE
<222> LOCATION: (7)..(7)
<223> OTHER INFORMATION: X = Thr, Ala or Met
<220> FEATURE:
<221> NAME/KEY: MISC_FEATURE
<222> LOCATION: (9)..(9)
<223> OTHER INFORMATION: X = Gln, Ala, Val or Arg
<220> FEATURE:
<221> NAME/KEY: MISC_FEATURE
<222> LOCATION: (11)..(11)
<223> OTHER INFORMATION: X = Ser or Asp
<220> FEATURE:
<221> NAME/KEY: MISC_FEATURE
<222> LOCATION: (12)..(12)
<223> OTHER INFORMATION: X = Gly, Phe or Ser
<220> FEATURE:
<221> NAME/KEY: MISC_FEATURE
<222> LOCATION: (13)..(13)
<223> OTHER INFORMATION: X = Gln, Lys or Val
<220> FEATURE:
<221> NAME/KEY: MISC_FEATURE
<222> LOCATION: (14)..(14)
<223> OTHER INFORMATION: X = Asp or Gly

<400> SEQUENCE: 72

Xaa Xaa Trp Xaa Xaa Gly Xaa Ala Xaa Gly Xaa Xaa Xaa Xaa
1               5                   10
```

```
<210> SEQ ID NO 73
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ser, Thr, Ala, Leu or Val
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Ala or Val
<220> FEATURE:
<221> NAME/KEY: MISC_FEATURE
<222> LOCATION: (7)..(7)
<223> OTHER INFORMATION: X = Glu, Asp, Ala, Val, His, Lys or Arg
<220> FEATURE:
<221> NAME/KEY: MISC_FEATURE
<222> LOCATION: (9)..(9)
<223> OTHER INFORMATION: X = Ser, Thr, Asp, Glu, Asn, Gly or Val

<400> SEQUENCE: 73

Trp Xaa Xaa Gly Xaa Xaa Xaa Gly Xaa
1               5

<210> SEQ ID NO 74
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Ser, Arg or Val
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = Ser, Leu, Val
<220> FEATURE:
<221> NAME/KEY: MISC_FEATURE
<222> LOCATION: (7)..(7)
<223> OTHER INFORMATION: X = Gln, Arg, Asn, Met, Trp or Asp
<220> FEATURE:
<221> NAME/KEY: MISC_FEATURE
<222> LOCATION: (8)..(8)
<223> OTHER INFORMATION: X = Ala, Val or Ser
<220> FEATURE:
<221> NAME/KEY: MISC_FEATURE
<222> LOCATION: (9)..(9)
<223> OTHER INFORMATION: X = Glu, Asp, Val or His
<220> FEATURE:
<221> NAME/KEY: MISC_FEATURE
<222> LOCATION: (11)..(11)
<223> OTHER INFORMATION: X = Ser, Asp, Glu, Asn, Val
<220> FEATURE:
<221> NAME/KEY: MISC_FEATURE
```

<222> LOCATION: (12)..(12)
<223> OTHER INFORMATION: X =Glu, Asp, Ser or Arg

<400> SEQUENCE: 74

Xaa Xaa Trp Xaa Xaa Gly Xaa Xaa Xaa Gly Xaa Xaa
1               5                   10

<210> SEQ ID NO 75
<211> LENGTH: 6
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(4)
<223> OTHER INFORMATION: X = any amino acid

<400> SEQUENCE: 75

Gly Xaa Ala Xaa Gly Ser
1               5

<210> SEQ ID NO 76
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Trp, His, Tyr or Val
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ser, Thr, Ala, Val or Leu
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Ala, Val, Leu, Cys or Glu
<220> FEATURE:
<221> NAME/KEY: MISC_FEATURE
<222> LOCATION: (7)..(7)
<223> OTHER INFORMATION: X = Glu, Asp, Lys, Arg or His
<220> FEATURE:
<221> NAME/KEY: MISC_FEATURE
<222> LOCATION: (9)..(9)
<223> OTHER INFORMATION: X = Ser, Thr, Gly, Val or Arg

<400> SEQUENCE: 76

Xaa Xaa Xaa Gly Xaa Xaa Xaa Gly Xaa
1               5

<210> SEQ ID NO 77
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE

```
<222> LOCATION: (1)..(1)
<223> OTHER INFORMATION: X = Leu or Arg
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Trp, His, Tyr or Val
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = Ser, Thr or Val
<220> FEATURE:
<221> NAME/KEY: MISC_FEATURE
<222> LOCATION: (7)..(7)
<223> OTHER INFORMATION: X = Lys, Arg, Asn, Glu or Leu
<220> FEATURE:
<221> NAME/KEY: MISC_FEATURE
<222> LOCATION: (8)..(8)
<223> OTHER INFORMATION: X = Ala, Val, Leu, Cys, Glu
<220> FEATURE:
<221> NAME/KEY: MISC_FEATURE
<222> LOCATION: (9)..(9)
<223> OTHER INFORMATION: X = Glu, Asp, Lys or Arg
<220> FEATURE:
<221> NAME/KEY: MISC_FEATURE
<222> LOCATION: (11)..(11)
<223> OTHER INFORMATION: X = Ser, Thr, Gly or Arg
<220> FEATURE:
<221> NAME/KEY: MISC_FEATURE
<222> LOCATION: (12)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = any amino acid
<220> FEATURE:
<221> NAME/KEY: MISC_FEATURE
<222> LOCATION: (14)..(14)
<223> OTHER INFORMATION: X = Leu, Arg, Pro, Gln or Trp

<400> SEQUENCE: 77

Xaa Xaa Xaa Xaa Xaa Gly Xaa Xaa Xaa Gly Xaa Xaa Xaa Xaa
1               5                   10

<210> SEQ ID NO 78
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(6)
<223> OTHER INFORMATION: X = any amino acid
<220> FEATURE:
<221> NAME/KEY: MISC_FEATURE
<222> LOCATION: (10)..(11)
<223> OTHER INFORMATION: X = any amino acid

<400> SEQUENCE: 78

Trp Xaa Xaa Xaa Xaa Xaa Ser Arg Gly Xaa Xaa Arg
1               5                   10

<210> SEQ ID NO 79
<211> LENGTH: 9
<212> TYPE: PRT
<213> ORGANISM: Artificial Sequence
<220> FEATURE:
```

```
<223> OTHER INFORMATION: consensus sequence
<220> FEATURE:
<221> NAME/KEY: MISC_FEATURE
<222> LOCATION: (1)..(1)
<223> OTHER INFORMATION: X = Trp, Phe or Lys
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Asn, Lys, His, Glu, Ser or Cys
<220> FEATURE:
<221> NAME/KEY: MISC_FEATURE
<222> LOCATION: (4)..(6)
<223> OTHER INFORMATION: X = any amino acid
<220> FEATURE:
<221> NAME/KEY: MISC_FEATURE
<222> LOCATION: (7)..(7)
<223> OTHER INFORMATION: X = Ser, Gly, Ile or Val
<220> FEATURE:
<221> NAME/KEY: MISC_FEATURE
<222> LOCATION: (8)..(8)
<223> OTHER INFORMATION: X = Ser, Thr, Lys, Arg or Trp
<220> FEATURE:
<221> NAME/KEY: MISC_FEATURE
<222> LOCATION: (9)..(9)
<223> OTHER INFORMATION: X = Gly, Ser, Glu or Lys

<400> SEQUENCE: 79

Xaa Xaa Xaa Xaa Xaa Xaa Xaa Xaa Xaa
1               5

<210> SEQ ID NO 80
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Trp or Phe
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Asn, His, Lys or Glu
<220> FEATURE:
<221> NAME/KEY: MISC_FEATURE
<222> LOCATION: (4)..(6)
<223> OTHER INFORMATION: X = any amino acid
<220> FEATURE:
<221> NAME/KEY: MISC_FEATURE
<222> LOCATION: (7)..(7)
<223> OTHER INFORMATION: X = Ser, Gly, Ile or Val
<220> FEATURE:
<221> NAME/KEY: MISC_FEATURE
<222> LOCATION: (8)..(8)
<223> OTHER INFORMATION: X = Ser, Thr, Lys or Arg
<220> FEATURE:
<221> NAME/KEY: MISC_FEATURE
<222> LOCATION: (9)..(9)
<223> OTHER INFORMATION: X = Gly or Lys
<220> FEATURE:
<221> NAME/KEY: MISC_FEATURE
<222> LOCATION: (10)..(10)
<223> OTHER INFORMATION: X = Gly, Glu, Ser or His
<220> FEATURE:
<221> NAME/KEY: MISC_FEATURE
<222> LOCATION: (11)..(11)
<223> OTHER INFORMATION: X = any amino acid
<220> FEATURE:
```

```
<221> NAME/KEY: MISC_FEATURE
<222> LOCATION: (12)..(12)
<223> OTHER INFORMATION: X = Arg, Lys, Leu or Gly

<400> SEQUENCE: 80

Xaa Xaa Xaa Xaa Xaa Xaa Xaa Xaa Xaa Xaa Xaa Xaa
1               5                   10

<210> SEQ ID NO 81
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Phe or Lys
<220> FEATURE:
<221> NAME/KEY: MISC_FEATURE
<222> LOCATION: (2)..(3)
<223> OTHER INFORMATION: X = any amino acid
<220> FEATURE:
<221> NAME/KEY: MISC_FEATURE
<222> LOCATION: (4)..(4)
<223> OTHER INFORMATION: X = Ser or Asp
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (8)..(8)
<223> OTHER INFORMATION: X = Arg or Trp
<220> FEATURE:
<221> NAME/KEY: MISC_FEATURE
<222> LOCATION: (9)..(9)
<223> OTHER INFORMATION: X = Gly, Ser or Glu
<220> FEATURE:
<221> NAME/KEY: MISC_FEATURE
<222> LOCATION: (10)..(10)
<223> OTHER INFORMATION: X = Gly, Glu or Pro
<220> FEATURE:
<221> NAME/KEY: MISC_FEATURE
<222> LOCATION: (11)..(11)
<223> OTHER INFORMATION: X = any amino acid
<220> FEATURE:
<221> NAME/KEY: MISC_FEATURE
<222> LOCATION: (12)..(12)
<223> OTHER INFORMATION: X = Arg or Lys

<400> SEQUENCE: 81

Xaa Xaa Xaa Xaa Xaa Xaa Ser Xaa Xaa Xaa Xaa Xaa
1               5                   10

<210> SEQ ID NO 82
<211> LENGTH: 11
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (10)..(10)
<223> OTHER INFORMATION: X = any amino acid

<400> SEQUENCE: 82
```

```
Arg Ser Xaa Ser Xaa Xaa Gly Gly Pro Xaa Glu
1               5                   10

<210> SEQ ID NO 83
<211> LENGTH: 8
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Arg or Asp
<220> FEATURE:
<221> NAME/KEY: MISC_FEATURE
<222> LOCATION: (2)..(2)
<223> OTHER INFORMATION: X = Ser, Thr, Phe or Leu
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (4)..(4)
<223> OTHER INFORMATION: X = Glu, Asp, Ser or Cys
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (8)..(8)
<223> OTHER INFORMATION: X = Gly, Cys, Ser or Lys

<400> SEQUENCE: 83

Xaa Xaa Xaa Xaa Xaa Xaa Gly Xaa
1               5

<210> SEQ ID NO 84
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (4)..(4)
<223> OTHER INFORMATION: X = Glu or Asp
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (8)..(8)
<223> OTHER INFORMATION: X = Gly or Cys
<220> FEATURE:
<221> NAME/KEY: MISC_FEATURE
<222> LOCATION: (9)..(10)
<223> OTHER INFORMATION: X = any amino acid
<220> FEATURE:
<221> NAME/KEY: MISC_FEATURE
<222> LOCATION: (11)..(11)
<223> OTHER INFORMATION: X = Glu, Asp or Arg
<220> FEATURE:
<221> NAME/KEY: MISC_FEATURE
<222> LOCATION: (12)..(12)
<223> OTHER INFORMATION: X = Val, Ala, Leu or Arg

<400> SEQUENCE: 84
```

```
Arg Ser Xaa Xaa Xaa Xaa Gly Xaa Xaa Xaa Xaa Xaa
1               5                   10
```

<210> SEQ ID NO 85
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Arg or Asp
<220> FEATURE:
<221> NAME/KEY: MISC_FEATURE
<222> LOCATION: (2)..(2)
<223> OTHER INFORMATION: X = Ser, Thr, Phe or Leu
<220> FEATURE:
<221> NAME/KEY: MISC_FEATURE
<222> LOCATION: (3)..(3)
<223> OTHER INFORMATION: X = Ser, Thr or Leu
<220> FEATURE:
<221> NAME/KEY: MISC_FEATURE
<222> LOCATION: (4)..(4)
<223> OTHER INFORMATION: X = Ser or Cys
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (8)..(8)
<223> OTHER INFORMATION: X = Gly, Cys, Ser or Lys
<220> FEATURE:
<221> NAME/KEY: MISC_FEATURE
<222> LOCATION: (9)..(9)
<223> OTHER INFORMATION: X = Pro, Glu or Ile
<220> FEATURE:
<221> NAME/KEY: MISC_FEATURE
<222> LOCATION: (10)..(10)
<223> OTHER INFORMATION: X = Met, Asn, Cys or Tyr
<220> FEATURE:
<221> NAME/KEY: MISC_FEATURE
<222> LOCATION: (11)..(11)
<223> OTHER INFORMATION: X = Glu, Asp, Val, Ser or Met
<220> FEATURE:
<221> NAME/KEY: MISC_FEATURE
<222> LOCATION: (12)..(12)
<223> OTHER INFORMATION: X = Val, Ala, Leu or His

<400> SEQUENCE: 85

```
Xaa Xaa Xaa Xaa Xaa Xaa Gly Xaa Xaa Xaa Xaa Xaa
1               5                   10
```

<210> SEQ ID NO 86
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(6)
<223> OTHER INFORMATION: X = any amino acid

<400> SEQUENCE: 86

```
Val Xaa Xaa Xaa Xaa Xaa Arg Glu Glu
1               5
```

<210> SEQ ID NO 87
<211> LENGTH: 6
<212> TYPE: PRT
<213> ORGANISM: Artificial Sequence
<220> FEATURE:

```
<223> OTHER INFORMATION: consensus sequence
<220> FEATURE:
<221> NAME/KEY: MISC_FEATURE
<222> LOCATION: (1)..(1)
<223> OTHER INFORMATION: X = Lys, Arg, Met, Gly or Asp
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Trp, Tyr, Ser, Thr, Phe or Ile
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = Arg, Asn, Ser, Thr or Leu
<220> FEATURE:
<221> NAME/KEY: MISC_FEATURE
<222> LOCATION: (6)..(6)
<223> OTHER INFORMATION: X = Lys, Arg, Glu, Asp or Leu

<400> SEQUENCE: 87

Xaa Xaa Xaa Xaa Xaa Xaa
1               5

<210> SEQ ID NO 88
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Asp or Gly
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Tyr, Gln, Thr or Gly
<220> FEATURE:
<221> NAME/KEY: MISC_FEATURE
<222> LOCATION: (4)..(4)
<223> OTHER INFORMATION: X = Glu, Trp, Gln or Leu
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = His, Arg, Ser or Cys
<220> FEATURE:
<221> NAME/KEY: MISC_FEATURE
<222> LOCATION: (7)..(7)
<223> OTHER INFORMATION: X = Lys or Arg
<220> FEATURE:
<221> NAME/KEY: MISC_FEATURE
<222> LOCATION: (8)..(8)
<223> OTHER INFORMATION: X = Lys, His, Ser, Thr
<220> FEATURE:
<221> NAME/KEY: MISC_FEATURE
<222> LOCATION: (9)..(9)
<223> OTHER INFORMATION: X = Ser, Thr, Phe or Ile
<220> FEATURE:
<221> NAME/KEY: MISC_FEATURE
<222> LOCATION: (10)..(10)
<223> OTHER INFORMATION: X = Leu, Val or Gln
<220> FEATURE:
```

```
<221> NAME/KEY: MISC_FEATURE
<222> LOCATION: (11)..(11)
<223> OTHER INFORMATION: X = Arg, Asn, Ser, Thr or Leu
<220> FEATURE:
<221> NAME/KEY: MISC_FEATURE
<222> LOCATION: (12)..(12)
<223> OTHER INFORMATION: X = Lys, Arg, Glu or Leu
<220> FEATURE:
<221> NAME/KEY: MISC_FEATURE
<222> LOCATION: (13)..(13)
<223> OTHER INFORMATION: X = Glu, Ala or Gly

<400> SEQUENCE: 88

Xaa Xaa Xaa Xaa Xaa Xaa Xaa Xaa Xaa Xaa Xaa Xaa Xaa
1               5                   10

<210> SEQ ID NO 89
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Val, Leu or Ile
<220> FEATURE:
<221> NAME/KEY: MISC_FEATURE
<222> LOCATION: (2)..(2)
<223> OTHER INFORMATION: X = Ser, Val or Ile
<220> FEATURE:
<221> NAME/KEY: MISC_FEATURE
<222> LOCATION: (3)..(3)
<223> OTHER INFORMATION: X = Lys, Arg, Met, Gly or Asp
<220> FEATURE:
<221> NAME/KEY: MISC_FEATURE
<222> LOCATION: (4)..(4)
<223> OTHER INFORMATION: X = Lys, His, Asn or Pro
<220> FEATURE:
<221> NAME/KEY: MISC_FEATURE
<222> LOCATION: (5)..(5)
<223> OTHER INFORMATION: X = Trp or Tyr
<220> FEATURE:
<221> NAME/KEY: MISC_FEATURE
<222> LOCATION: (6)..(6)
<223> OTHER INFORMATION: X = any amino acid
<220> FEATURE:
<221> NAME/KEY: MISC_FEATURE
<222> LOCATION: (7)..(7)
<223> OTHER INFORMATION: X = Arg or Asn
<220> FEATURE:
<221> NAME/KEY: MISC_FEATURE
<222> LOCATION: (8)..(8)
<223> OTHER INFORMATION: X = Glu or Asp
<220> FEATURE:
<221> NAME/KEY: MISC_FEATURE
<222> LOCATION: (9)..(9)
<223> OTHER INFORMATION: X = Glu, Cys or Pro

<400> SEQUENCE: 89

Xaa Xaa Xaa Xaa Xaa Xaa Xaa Xaa Xaa
1               5

<210> SEQ ID NO 90
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (3)..(6)
<223> OTHER INFORMATION: X = any amino acid
<220> FEATURE:
<221> NAME/KEY: MISC_FEATURE
```

<222> LOCATION: (9)..(9)
<223> OTHER INFORMATION: X = any amino acid

<400> SEQUENCE: 90

Val Gly Xaa Xaa Xaa Xaa Trp Pro Xaa Val Arg Glu
1               5                   10

<210> SEQ ID NO 91
<211> LENGTH: 11
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Gly, Ala or Ser
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ala, Val, Ile, Arg, Glu or Gln
<220> FEATURE:
<221> NAME/KEY: MISC_FEATURE
<222> LOCATION: (4)..(4)
<223> OTHER INFORMATION: X = Lys, Ser, Thr, Ala, Gly or Glu
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Trp or Leu
<220> FEATURE:
<221> NAME/KEY: MISC_FEATURE
<222> LOCATION: (7)..(7)
<223> OTHER INFORMATION: X = Pro, Asp, Glu, Ala, Gly or Ser
<220> FEATURE:
<221> NAME/KEY: MISC_FEATURE
<222> LOCATION: (8)..(10)
<223> OTHER INFORMATION: X = any amino acid
<220> FEATURE:
<221> NAME/KEY: MISC_FEATURE
<222> LOCATION: (11)..(11)
<223> OTHER INFORMATION: X = Glu, Ser, Leu, Lys or Ala

<400> SEQUENCE: 91

Xaa Xaa Xaa Xaa Xaa Xaa Xaa Xaa Xaa Xaa Xaa
1               5                   10

<210> SEQ ID NO 92
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Gly or Ala
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ala, Val or Arg
<220> FEATURE:
<221> NAME/KEY: MISC_FEATURE
<222> LOCATION: (4)..(4)

```
<223> OTHER INFORMATION: X = Lys or Ser
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = Trp or Leu
<220> FEATURE:
<221> NAME/KEY: MISC_FEATURE
<222> LOCATION: (7)..(7)
<223> OTHER INFORMATION: X = Pro or Ala
<220> FEATURE:
<221> NAME/KEY: MISC_FEATURE
<222> LOCATION: (8)..(8)
<223> OTHER INFORMATION: X = Asn or Glu
<220> FEATURE:
<221> NAME/KEY: MISC_FEATURE
<222> LOCATION: (11)..(11)
<223> OTHER INFORMATION: X = Ser or Leu
<220> FEATURE:
<221> NAME/KEY: MISC_FEATURE
<222> LOCATION: (12)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = Glu or Gln

<400> SEQUENCE: 92

Xaa Xaa Xaa Xaa Xaa Xaa Xaa Xaa Cys Gly Xaa Xaa Xaa
1               5                   10

<210> SEQ ID NO 93
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Gly or Ser
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = Ala, Val, Glu or Gln
<220> FEATURE:
<221> NAME/KEY: MISC_FEATURE
<222> LOCATION: (4)..(4)
<223> OTHER INFORMATION: X = Ala, Lys or Glu
<220> FEATURE:
<221> NAME/KEY: MISC_FEATURE
<222> LOCATION: (5)..(5)
<223> OTHER INFORMATION: X = any amino acid
<220> FEATURE:
<221> NAME/KEY: MISC_FEATURE
<222> LOCATION: (7)..(7)
<223> OTHER INFORMATION: X = Pro, Asp or Glu
<220> FEATURE:
<221> NAME/KEY: MISC_FEATURE
<222> LOCATION: (8)..(8)
<223> OTHER INFORMATION: X = Ile, Glu, Arg, Ser or Thr
<220> FEATURE:
<221> NAME/KEY: MISC_FEATURE
<222> LOCATION: (9)..(9)
<223> OTHER INFORMATION: X = Ile, Val or Lys
<220> FEATURE:
<221> NAME/KEY: MISC_FEATURE
<222> LOCATION: (10)..(10)
<223> OTHER INFORMATION: X = Arg, Ala or Gly
<220> FEATURE:
```

```
<221> NAME/KEY: MISC_FEATURE
<222> LOCATION: (11)..(11)
<223> OTHER INFORMATION: X = Glu or Leu
<220> FEATURE:
<221> NAME/KEY: MISC_FEATURE
<222> LOCATION: (12)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = Glu, Gln, Leu or Met

<400> SEQUENCE: 93

Xaa Xaa Xaa Xaa Xaa Trp Xaa Xaa Xaa Xaa Xaa Xaa Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Val, Gln or Glu
<220> FEATURE:
<221> NAME/KEY: MISC_FEATURE
<222> LOCATION: (2)..(2)
<223> OTHER INFORMATION: X = Glu, Gly, Thr or Val
<220> FEATURE:
<221> NAME/KEY: MISC_FEATURE
<222> LOCATION: (3)..(3)
<223> OTHER INFORMATION: X = Lys, Leu, Val or His
<220> FEATURE:
<221> NAME/KEY: MISC_FEATURE
<222> LOCATION: (5)..(5)
<223> OTHER INFORMATION: X = Pro, Ser, Asp, Glu or Gly
<220> FEATURE:
<221> NAME/KEY: MISC_FEATURE
<222> LOCATION: (6)..(6)
<223> OTHER INFORMATION: X = Ile, Ala, Val, Glu, Arg, Ser or Thr
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (8)..(8)
<223> OTHER INFORMATION: X = Lys, Val, Thr or Asp
<220> FEATURE:
<221> NAME/KEY: MISC_FEATURE
<222> LOCATION: (9)..(9)
<223> OTHER INFORMATION: X = Glu, Lys or Ala
<220> FEATURE:
<221> NAME/KEY: MISC_FEATURE
<222> LOCATION: (10)..(10)
<223> OTHER INFORMATION: X = Val, Ser, Thr, Pro or Glu
<220> FEATURE:
<221> NAME/KEY: MISC_FEATURE
<222> LOCATION: (11)..(11)
<223> OTHER INFORMATION: X = Ser, Val or Trp

<400> SEQUENCE: 94

Xaa Xaa Xaa Trp Xaa Xaa Xaa Xaa Xaa Xaa Xaa
1               5                   10

<210> SEQ ID NO 95
<211> LENGTH: 10
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
```

```
<222> LOCATION: (1)..(1)
<223> OTHER INFORMATION: X = Val or Ile
<220> FEATURE:
<221> NAME/KEY: MISC_FEATURE
<222> LOCATION: (2)..(2)
<223> OTHER INFORMATION: X = Ser or Thr
<220> FEATURE:
<221> NAME/KEY: MISC_FEATURE
<222> LOCATION: (3)..(3)
<223> OTHER INFORMATION: X = Leu or Lys
<220> FEATURE:
<221> NAME/KEY: MISC_FEATURE
<222> LOCATION: (5)..(5)
<223> OTHER INFORMATION: X = Asp or Glu
<220> FEATURE:
<221> NAME/KEY: MISC_FEATURE
<222> LOCATION: (6)..(6)
<223> OTHER INFORMATION: X = any amino acid

<400> SEQUENCE: 95

Xaa Xaa Xaa Trp Xaa Xaa Gly Leu Ala Glu
1               5                   10

<210> SEQ ID NO 96
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (9)..(9)
<223> OTHER INFORMATION: X = any amino acid
<220> FEATURE:
<221> NAME/KEY: MISC_FEATURE
<222> LOCATION: (11)..(12)
<223> OTHER INFORMATION: X = any amino acid

<400> SEQUENCE: 96

Val Xaa Leu Xaa Ser Ala Xaa Lys Xaa Tyr Xaa Xaa Val
1               5                   10

<210> SEQ ID NO 97
<211> LENGTH: 12
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Glu, Asp, Val or Ala
<220> FEATURE:
<221> NAME/KEY: MISC_FEATURE
<222> LOCATION: (2)..(2)
<223> OTHER INFORMATION: X = Pro, Gln, Asn, Glu, Arg, Leu or Cys
<220> FEATURE:
<221> NAME/KEY: MISC_FEATURE
<222> LOCATION: (3)..(3)
<223> OTHER INFORMATION: X = Ile, Ala, Val, Ser or Thr
<220> FEATURE:
<221> NAME/KEY: MISC_FEATURE
<222> LOCATION: (4)..(4)
```

```
<223> OTHER INFORMATION: X = Ser, Thr or Ala
<220> FEATURE:
<221> NAME/KEY: MISC_FEATURE
<222> LOCATION: (5)..(5)
<223> OTHER INFORMATION: X = Ala, Thr
<220> FEATURE:
<221> NAME/KEY: MISC_FEATURE
<222> LOCATION: (6)..(6)
<223> OTHER INFORMATION: X = His, Lys, Arg or Gln
<220> FEATURE:
<221> NAME/KEY: MISC_FEATURE
<222> LOCATION: (7)..(7)
<223> OTHER INFORMATION: X = Ser, Lys or Gly
<220> FEATURE:
<221> NAME/KEY: MISC_FEATURE
<222> LOCATION: (8)..(8)
<223> OTHER INFORMATION: X = Arg, Ser or Cys
<220> FEATURE:
<221> NAME/KEY: MISC_FEATURE
<222> LOCATION: (9)..(9)
<223> OTHER INFORMATION: X = Tyr, Ala, Ile or Val
<220> FEATURE:
<221> NAME/KEY: MISC_FEATURE
<222> LOCATION: (10)..(11)
<223> OTHER INFORMATION: X =  any amino acid
<220> FEATURE:
<221> NAME/KEY: MISC_FEATURE
<222> LOCATION: (12)..(12)
<223> OTHER INFORMATION: X =  Val, Ala or Met

<400> SEQUENCE: 97

Xaa Xaa Xaa Xaa Xaa Xaa Xaa Xaa Xaa Xaa Xaa Xaa
1               5                   10

<210> SEQ ID NO 98
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Glu or Val
<220> FEATURE:
<221> NAME/KEY: MISC_FEATURE
<222> LOCATION: (2)..(2)
<223> OTHER INFORMATION: X = Pro or Gln
<220> FEATURE:
<221> NAME/KEY: MISC_FEATURE
<222> LOCATION: (3)..(3)
<223> OTHER INFORMATION: X = Leu or Cys
<220> FEATURE:
<221> NAME/KEY: MISC_FEATURE
<222> LOCATION: (4)..(4)
<223> OTHER INFORMATION: X = Ile, Ala or Val
<220> FEATURE:
<221> NAME/KEY: MISC_FEATURE
<222> LOCATION: (5)..(5)
<223> OTHER INFORMATION: X = Ser, Thr or Ala
<220> FEATURE:
<221> NAME/KEY: MISC_FEATURE
<222> LOCATION: (7)..(7)
<223> OTHER INFORMATION: X = His, Lys or Arg
<220> FEATURE:
<221> NAME/KEY: MISC_FEATURE
<222> LOCATION: (9)..(9)
<223> OTHER INFORMATION: X = Arg or Ser
<220> FEATURE:
<221> NAME/KEY: MISC_FEATURE
<222> LOCATION: (11)..(12)
<223> OTHER INFORMATION: X = any amino acid

<400> SEQUENCE: 98

Xaa Xaa Xaa Xaa Xaa Ala Xaa Lys Xaa Tyr Xaa Xaa Val
1               5                   10
```

```
<210> SEQ ID NO 99
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: X = Glu or Val
<220> FEATURE:
<221> NAME/KEY: MISC_FEATURE
<222> LOCATION: (2)..(2)
<223> OTHER INFORMATION: X = Glu, Arg or Gln
<220> FEATURE:
<221> NAME/KEY: MISC_FEATURE
<222> LOCATION: (3)..(3)
<223> OTHER INFORMATION: X = Leu or Cys
<220> FEATURE:
<221> NAME/KEY: MISC_FEATURE
<222> LOCATION: (4)..(4)
<223> OTHER INFORMATION: X = Val or Ser
<220> FEATURE:
<221> NAME/KEY: MISC_FEATURE
<222> LOCATION: (5)..(5)
<223> OTHER INFORMATION: X = Ser, Thr or Ala
<220> FEATURE:
<221> NAME/KEY: MISC_FEATURE
<222> LOCATION: (6)..(6)
<223> OTHER INFORMATION: X = Ala or Thr
<220> FEATURE:
<221> NAME/KEY: MISC_FEATURE
<222> LOCATION: (7)..(7)
<223> OTHER INFORMATION: X = Arg or Gln
<220> FEATURE:
<221> NAME/KEY: MISC_FEATURE
<222> LOCATION: (8)..(8)
<223> OTHER INFORMATION: X = Ser, Lys or Gly
<220> FEATURE:
<221> NAME/KEY: MISC_FEATURE
<222> LOCATION: (9)..(9)
<223> OTHER INFORMATION: X = Arg, Ser or Cys
<220> FEATURE:
<221> NAME/KEY: MISC_FEATURE
<222> LOCATION: (10)..(10)
<223> OTHER INFORMATION: X = Ala, Ile or Val
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = Val or Met

<400> SEQUENCE: 99

Xaa Xaa Xaa Xaa Xaa Xaa Xaa Xaa Xaa Xaa Xaa Xaa Xaa
1               5                   10

<210> SEQ ID NO 100
<211> LENGTH: 12
<212> TYPE: PRT
<213> ORGANISM: Artificial Sequence
<220> FEATURE:
<223> OTHER INFORMATION: epitope

<400> SEQUENCE: 100

Thr Arg Trp Gln Lys Gly Leu Ala Leu Gly Ser Gly
1               5                   10

<210> SEQ ID NO 101
<211> LENGTH: 12
<212> TYPE: PRT
```

```
<213> ORGANISM: Artificial Sequence
<220> FEATURE:
<223> OTHER INFORMATION: shortened peptide binding to trastuzumab

<400> SEQUENCE: 101

Gly Arg Trp Ser Glu Gly Thr Ala Leu Gly Ser Ser
1 5 10

<210> SEQ ID NO 102
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 102

Gly Gln Trp Ala Arg Gly Leu Ala Val Gly Ser Cys
1 5 10

<210> SEQ ID NO 103
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 103

Gly Thr Trp Glu Arg Gly Val Ala Ala Gly Asp Ile
1 5 10

<210> SEQ ID NO 104
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 104

Thr Leu Trp His Arg Gly Leu Ala Ala Gly Asp Val
1 5 10

<210> SEQ ID NO 105
<211> LENGTH: 11
<212> TYPE: PRT
<213> ORGANISM: Artificial Sequence
<220> FEATURE:
<223> OTHER INFORMATION: shortened peptide binding to trastuzumab

<400> SEQUENCE: 105

Ser Trp Ala Ser Gly Met Ala Val Gly Ser Val
1 5 10

<210> SEQ ID NO 106
<211> LENGTH: 10
<212> TYPE: PRT
<213> ORGANISM: Artificial Sequence
<220> FEATURE:
<223> OTHER INFORMATION: shortened peptide binding to trastuzumab

<400> SEQUENCE: 106

Trp Ala Phe Gly Leu Ala Leu Gly Ser Leu
1 5 10

<210> SEQ ID NO 107
<211> LENGTH: 11
<212> TYPE: PRT
<213> ORGANISM: Artificial Sequence
```

```
<220> FEATURE:
<223> OTHER INFORMATION: shortened peptide binding to trastuzumab

<400> SEQUENCE: 107

Gln Tr

<223> OTHER INFORMATION: shortened peptide binding to trastuzumab

<400> SEQUENCE: 113

Cys Gln Trp Arg Ala Gly Thr Ala Val Gly Ser Ser Val Gly
1 5 10

<210> SEQ ID NO 114
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 114

Arg Thr Trp Gln Ser Gly Met Ala Asp Gly Glu Glu
1 5 10

<210> SEQ ID NO 115
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 115

Ser Leu Trp Leu Leu Gly Arg Ala Asp Gly Val Ser
1 5 10

<210> SEQ ID NO 116
<211> LENGTH: 10
<212> TYPE: PRT
<213> ORGANISM: Artificial Sequence
<220> FEATURE:
<223> OTHER INFORMATION: shortened peptide binding to trastuzumab

<400> SEQUENCE: 116

Trp Met Ser Gly Gln Ser Asp Gly Ser Ser
1 5 10

<210> SEQ ID NO 117
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 117

Val Ala Trp Ser Ser Gly Gln Ala His Gly Ser Arg
1 5 10

<210> SEQ ID NO 118
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 118

Ser Ala Trp Leu Leu Gly Asn Val Glu Gly Ser Glu
1 5 10

<210> SEQ ID NO 119
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 119

Ser Gly Trp Ser Val Gly Trp Ala Asp Gly Asp Asp
1               5                   10

<210> SEQ ID NO 120
<211> LENGTH: 10
<212> TYPE: PRT
<213> ORGANISM: Artificial Sequence
<220> FEATURE:
<223> OTHER INFORMATION: shortened peptide binding to trastuzumab

<400> SEQUENCE: 120

Trp Asp Ser Gly Asp Ala Val Gly Asn Glu
1               5                   10

<210> SEQ ID NO 121
<211> LENGTH: 14
<212> TYPE: PRT
<213> ORGANISM: Artificial Sequence
<220> FEATURE:
<223> OTHER INFORMATION: shortened peptide binding to trastuzumab

<400> SEQUENCE: 121

Leu Lys Trp Tyr Ser Gly Glu Leu Glu Gly Ser Lys Glu Leu
1               5                   10

<210> SEQ ID NO 122
<211> LENGTH: 14
<212> TYPE: PRT
<213> ORGANISM: Artificial Sequence
<220> FEATURE:
<223> OTHER INFORMATION: shortened peptide binding to trastuzumab

<400> SEQUENCE: 122

Leu Ser His Thr Ser Gly Arg Val Glu Gly Ser Val Ser Leu
1 5 10

<210> SEQ ID NO 123
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 123

Gly Trp Asn Ser Gly Lys Val Asp Gly Gly Ala Gly Arg
1 5 10

<210> SEQ ID NO 124
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 124

Tyr Phe Ser Gly Lys Ala Glu Gly Arg Glu Ala Pro
1 5 10

<210> SEQ ID NO 125
<211> LENGTH: 11
<212> TYPE: PRT
<213> ORGANISM: Artificial Sequence
<220> FEATURE:
<223> OTHER INFORMATION: shortened peptide binding to trastuzumab

```
<400> SEQUENCE: 125

Val Thr Gly Asn Cys Lys Gly Ser Arg Gln Gln
1 5 10

<210> SEQ ID NO 126
<211> LENGTH: 14
<212> TYPE: PRT
<213> ORGANISM: Artificial Sequence
<220> FEATURE:
<223> OTHER INFORMATION: shortened peptide binding to trastuzumab

<400> SEQUENCE: 126

Arg Leu Val Pro Val Gly Leu Glu Arg Gly Thr Val Asp Trp
1 5 10

<210> SEQ ID NO 127
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 127

Trp Gly Glu Pro Tyr Ser Gly Lys Gly Ser His Gly
1 5 10

<210> SEQ ID NO 128
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 128

Trp Gly Asn Cys Pro Leu Ser Ser Gly Gly Pro Lys
1 5 10

<210> SEQ ID NO 129
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 129

Trp Arg His Lys His Ile Val Thr Lys Gly Gly Leu
1 5 10

<210> SEQ ID NO 130
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 130

Trp Ala His Gly Glu Asp Ile Thr Gly His Ser Leu
1 5 10

<210> SEQ ID NO 131
<211> LENGTH: 12
<212> TYPE: PRT
<213> ORGANISM: Artificial sequence
<220> FEATURE:
<223> OTHER INFORMATION: shortened peptide binding to trastuzumab

<400> SEQUENCE: 131
```

```
Phe Pro Lys Ser Gln Val Ser Arg Gly Glu Met Arg
1               5                   10
```

<210> SEQ ID NO 132
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 132

```
Lys Asn Cys Asp Arg Leu Ser Trp Ser Gly Ala Arg
1               5                   10
```

<210> SEQ ID NO 133
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 133

Phe Leu Ser Asp Lys Tyr Ser Arg Glu Pro His Lys
1 5 10

<210> SEQ ID NO 134
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 134

Arg Ser Phe Glu Lys Phe Gly Gly Met Lys Glu Arg
1 5 10

<210> SEQ ID NO 135
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 135

Arg Ser Asn Asp Val Leu Gly Cys Lys Leu Arg Val
1 5 10

<210> SEQ ID NO 136
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 136

Asp Ser Thr Ser Leu Ala Gly Gly Pro Tyr Glu Ala
1 5 10

<210> SEQ ID NO 137
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 137

```
Arg Leu Ser Ser Ala Gln Gly Cys Ile Asn Met Val
1               5                   10
```

<210> SEQ ID NO 138
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 138

```
Arg Thr Leu Cys Gly Thr Gly Ser Glu Met Val Leu
1               5                   10
```

<210> SEQ ID NO 139
<211> LENGTH: 12
<212> TYPE: PRT
<213> ORGANISM: Artificial Sequence
<220> FEATURE:
<223> OTHER INFORMATION: shortened peptide binding to trastuzumab

<400> SEQUENCE: 139

Arg Phe Ser Cys Ala Val Gly Lys Glu Cys Ser His
1 5 10

<210> SEQ ID NO 140
<211> LENGTH: 10
<212> TYPE: PRT
<213> ORGANISM: Artificial sequence
<220> FEATURE:
<223> OTHER INFORMATION: shortened peptide binding to trastuzumab

<400> SEQUENCE: 140

Leu Ser Arg Cys Gly Lys Pro Met Asp Val
1 5 10

<210> SEQ ID NO 141
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 141

Asp Val Thr Trp Arg His Lys His Ile Val Thr Lys Gly
1 5 10

<210> SEQ ID NO 142
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 142

Gly Gly Tyr Glu Val Arg Lys His Phe Gln Ser Arg Glu
1 5 10

<210> SEQ ID NO 143
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 143

Asp Pro Tyr Glu Ser Ser Arg Ser Thr Leu Leu Arg Ala

```
1               5                    10

<210> SEQ ID NO 144
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 144

Asp Val Gly Gln Gly Arg Ar

<210> SEQ ID NO 150
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 150

Gly Ser Arg Ser Met Trp Ala Glu Cys Gly Leu Asp Glu
1 5 10

<210> SEQ ID NO 151
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 151

Gly Val Val Lys Ala Trp Asp Ser Ile Arg Leu Val Glu
1 5 10

<210> SEQ ID NO 152
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 152

Gly Asp Glu Glu Met Trp Pro Ile Val Arg Glu Leu Gln
1 5 10

<210> SEQ ID NO 153
<211> LENGTH: 13
<212> TYPE: PRT
<213> ORGANISM: Artificial sequence
<220> FEATURE:
<223> OTHER INFORMATION: peptide binding to trastuzumab

<400> SEQUENCE: 153

Gly Ala Ala Ala Gln Trp Pro Glu Val Arg Glu Tyr Leu
1 5 10

<210> SEQ ID NO 154
<211> LENGTH: 13
<212> TYPE: PRT
<213> ORGANISM: Artificial sequence
<220> FEATURE:
<223> OTHER INFORMATION: peptide binding to trastuzumab

<400> SEQUENCE: 154

Ser Val Gln Lys Lys Trp Glu Arg Lys Ala Glu Ser Met
1 5 10

<210> SEQ ID NO 155
<211> LENGTH: 11
<212> TYPE: PRT
<213> ORGANISM: Artificial Sequence
<220> FEATURE:
<223> OTHER INFORMATION: shortened peptide binding to trastuzumab

<400> SEQUENCE: 155

Val Glu His Trp Ser Arg Ser Lys Lys Ser Ser
1 5 10

<210> SEQ ID NO 156
<211> LENGTH: 11
<212> TYPE: PRT
<213> ORGANISM: Artificial Sequence
<220> FEATURE:
<223> OTHER INFORMATION: shortened peptide binding to trastuzumab

<400> SEQUENCE: 156

Val Gly Val Trp Pro Val Met Val Glu Thr Val
1               5                   10

<210> SEQ ID NO 157
<211> LENGTH: 11
<212> TYPE: PRT
<213> ORGANISM: Artificial sequence
<220> FEATURE:
<223> OTHER INFORMATION: peptide binding to trastuzumab

<400> SEQUENCE: 157

Gln Thr Lys Trp Pro Ile Ala Thr Glu Val Trp
1               5                   10

<210> SEQ ID NO 158
<211> LENGTH: 11
<212> TYPE: PRT
<213> ORGANISM: Artificial Sequence
<220> FEATURE:
<223> OTHER INFORMATION: shortened peptide binding to trastuzumab

<400> SEQUENCE: 158

Glu Val Leu Trp Gly Glu Met Asp Ala Pro Trp
1               5                   10

<210> SEQ ID NO 159
<211> LENGTH: 10
<212> TYPE: PRT
<213> ORGANISM: Artificial sequence
<220> FEATURE:
<223> OTHER INFORMATION: peptide binding to trastuzumab

<400> SEQUENCE: 159

Val Thr Leu Trp Glu Thr Gly Leu Ala Glu
1               5                   10

<210> SEQ ID NO 160
<211> LENGTH: 10
<212> TYPE: PRT
<213> ORGANISM: Artificial Sequence
<220> FEATURE:
<223> OTHER INFORMATION: shortened peptide binding to trastuzumab

<400> SEQUENCE: 160

Ile Ser Lys Trp Asp Ala Gly Leu Ala Glu
1               5                   10

<210> SEQ ID NO 161
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 161

Glu Pro Cys Ile Thr Ala His Lys Ser Tyr Met Arg Val
1               5                   10

<210> SEQ ID NO 162
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 162

Val Gln Leu Ala Ser Ala Lys Lys Arg Tyr Leu Gly Val
1 5 10

<210> SEQ ID NO 163
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 163

Glu Glu Leu Val Ala Thr Arg Ser Arg Ala Gly Gly Met
1 5 10

<210> SEQ ID NO 164
<211> LENGTH: 13
<212> TYPE: PRT
<213> ORGANISM: Artificial Sequence
<220> FEATURE:
<223> OTHER INFORMATION: shortened peptide binding to trastuzumab

<400> SEQUENCE: 164

Val Arg Leu Ser Ser Ala Gln Gly Cys Ile Asn Met Val
1 5 10

<210> SEQ ID NO 165
<211> LENGTH: 15
<212> TYPE: PRT
<213> ORGANISM: Artificial Sequence
<220> FEATURE:
<223> OTHER INFORMATION: shortened peptide binding to trastuzumab

<400> SEQUENCE: 165

Ser Glu Ser Gly Val Phe Val Leu Gln Ser Cys Ala Trp Glu Tyr
1 5 10 15

<210> SEQ ID NO 166
<211> LENGTH: 15
<212> TYPE: PRT
<213> ORGANISM: Artificial Sequence
<220> FEATURE:
<223> OTHER INFORMATION: shortened peptide binding to trastuzumab

<400> SEQUENCE: 166

Ser Cys Leu Ala Arg Val His Cys Asp Met Pro Arg Glu Trp Glu
1 5 10 15

<210> SEQ ID NO 167
<211> LENGTH: 24
<212> TYPE: DNA
<213> ORGANISM: Artificial Sequence
<220> FEATURE:
<223> OTHER INFORMATION: sequence of the AAV2 library at N587

<400> SEQUENCE: 167
tccggagcac aagcagctac cgca 24

-continued

```
<210> SEQ ID NO 168
<211> LENGTH: 8
<212> TYPE: PRT
<213> ORGANISM: Artificial Sequence
<220> FEATURE:
<223> OTHER INFORMATION: sequence of the AAV2 library at N587

<400> SEQUENCE: 168

Ser Gly Ala Gln Ala Ala Thr Cys
1               5
```

ANTI-HER2 VACCINE BASED UPON AAV DERIVED MULTIMERIC STRUCTURES

CROSS-REFERENCE TO PRIOR APPLICATIONS

This application is a U.S. National Phase Application of International Application No. PCT/EP2012/068110, filed Sep. 14, 2012, which claims the benefit of U.S. Application No. 61/535,124, filed Sep. 15, 2011, both of which are hereby incorporated by reference in their entirety.

SEQUENCE LISTING INFORMATION

A computer readable text file, entitled "M147-0015-Sequence Listing.txt" created on or about Jun. 27, 2017, with a file size of about 58.3 KB, contains the sequence listing for this application and is hereby incorporated by reference in its entirety.

The present invention relates to parvovirus mutated structural proteins comprising insertions of mimotopes of a HER2, compositions, multimeric structures, medicaments and vaccines comprising the same, nucleic acids, expression cassettes, constructs, vectors and cells comprising the nucleic acids, methods of preparing the structural proteins and methods of inducing a B-cell response or of treating a HER2-related disease.

The human epidermal growth factor receptor (HER2, also referred to as Her-2, HER-2/neu, c-erbB-2) is a transmembrane protein and member of the human epidermal growth factor receptor (EGFR) family. HER2 gene amplification is associated with over-expression of the HER2 protein and has been associated with increased cell proliferation, cell motility, tumor invasiveness, progressive regional and distant metastases, accelerated angiogenesis, and reduced apoptosis (Ross et al. 2009). Beyond breast cancer, HER2 over-expression/amplification is associated with ovarian, bladder, salivary gland, endometrial, pancreatic and non-small-cell lung cancer (Hynes et al. 1994; Scholl et al. 2001).

Accordingly, HER2 has become one of the most prominent cancer targets addressed by a number of monoclonal antibody therapies. Trastuzumab is a monoclonal antibody that binds with high affinity to the extracellular domain of HER2 and has demonstrated clinical benefits in tumor patients with tumors having gene amplification of HER2 as monotherapy and in combination with chemotherapy (Slamon et al. 2001; Harries and Smith 2002; Vogel et al. 2002). Pertuzumab is a humanized monoclonal antibody directed against the extracellular dimerization domain II of HER2 that has shown modest antitumor activity in unselected patients and seems to have synergistic antitumor activity in combination with trastuzumab (Müller et al. 2009). Further anti-HER2 antibodies in clinical development are MDX-H210, 2B1, C6.5xscFv(NM3E2), ertumaxomab and FRP-5 derivates (Friedlander et al. 2008).

Despite these advances with passive immunotherapies using anti-HER2 monoclonal antibodies, there remain a number of concerns such as repeated treatments and associated costs, limited duration of therapeutic effectiveness, and possibly undesired immunogenicity. Accordingly, it has been reported that usually drug resistance can be observed within one year from the beginning of treatment in the metastatic setting (Nahta and Esteva 2006). Furthermore, cardiac toxicity has been reported as a side effect of the treatment.

Therefore, a therapeutic approach capable of inducing active specific immunity would prove to be highly advantageous, offering sustained protection at a lower cost, preventive therapy e.g. for high risk individuals, and long term immunity. However, cancer vaccines targeting self tumor antigens such as HER2 must overcome immunological tolerance. Substantial evidence exists that immunizing with peptides derived from self-antigens may be an effective means of circumventing tolerance (Disis et al. 1999). Various concepts of HER2 vaccines exist. In principle one can distinguish between vaccination strategies aiming at B-cell responses directed against the extracellular domain of HER2 or strategies aiming at T-cell responses against extracellular or intracellular portions of the HER2 protein.

Disis et al. (1999; 2002; 2009) have focused on eliciting CD4+ T-helper responses using longer HER2 peptides with a length of 15 to 18 amino acids in order to augment the preexistent HER2 specific immune response detected in patients, resulting in augmented HER2 antibodies and/or HER2 specific cytotoxic T cells, both of which can mediate an antitumor response.

Peoples et al. (2008) have pursued a similar approach using the E75 peptide (369-377 from HER2) to recruit CD4 helper T cells in an adjuvant setting indicating safety and efficacy at stimulating HER2-specific immunity measured as a dose-dependent enhancement of DTH reactions in vaccinated patients. However, the vaccinated patients were at higher risk for recurrence than the observed patients, which is attributed to the different steroid hormone receptor status in the two groups. On the other hand despite the higher incidence of visceral metastases among vaccinated patients, the death rate was substantially lower, suggesting a potential clinical benefit to the vaccine. Still, this therapy is obviously restricted to HLA-A2 and HLA-A3 positive patients and therefore is only applicable to roughly 50% of the patients.

Reilly et al. (Reilly et al. 2000) have tested a whole-cell vaccine in a mouse model using the HER2 rat homologue neu. neu-specific vaccination of transgenic mice elicited an antibody response and resulted in an increase in neu-specific T cells leading to a delayed spontaneous tumor growth despite tolerance to the tumor antigen.

Ercolini et al. (2003) have used an adoptive therapy approach in a mouse model using the $RNEU_{420-429}$ peptide, which is the dominant target of the CD8+ T cell response in FVB/N mice. Vaccination with the $RNEU_{420-429}$ peptide pulsed onto dendritic cells and transferred into FVB/N mice did not demonstrate antitumor immunity. However, vaccinating FVB/N mice with dendritic cells pulsed with a heteroclitic variant of the wild-type epitope induces improved protection against tumors that express the natural $RNEU_{420-429}$ epitope as compared with immunization with the $RNEU_{420-429}$ epitope itself neu-N mice showed a promising trend toward protection when vaccinated with the heteroclitic peptide but not to the degree seen in FVB/N mice, which is interpreted as being due to the neu-specific tolerance seen in neu-N mice. The authors conclude that the tested regimen proved to be far less efficacious than a whole-cell vaccine, supporting the concept that vaccines that induce both CTL and Th cell responses may be more effective than vaccines that only enhance the CTL response.

Generally, major drawbacks of this kind of peptide vaccination are the generally low immunogenicity of peptides, the HLA restriction and the necessity of a preexisting immune response against HER2 in patients. Furthermore, it can be envisaged that the induction of a CD4 helper dependent immune reaction may be compromised in patients who are co-treated with chemotherapy which suppresses the immune system. Still, these findings have important implications in HER2 cancer therapy: they suggest that vaccination may be an effective means of either initiating or boosting antitumor immunity. Equally promising, the autoimmunity provoked by vaccination seems to be tumor-restricted as signs of autoimmune disease are not detected in other tissues expressing physiological levels of HER2 (Disis et al. 1996; Disis et al. 2002; Jasinska et al. 2003).

The other vaccination strategy against HER2 aims at induction of B-cell responses directed against the extracellular domain of HER2 by a B-cell vaccine.

Esserman et al. (1999) used the extracellular domain of neu in order to immunize neu-transgenic mice, which developed a neu-specific humoral immune response. Subsequent development of mammary tumors was significantly lower in immunized mice versus control, which translated into an increase in median survival.

Dakappagari et al. (2000) reported the anti-tumor properties of a chimeric B-cell epitope sequence 628-647 that incorporates a promiscuous T-cell epitope derived from a measles virus protein (MVF). Synthetic peptides of the extracellular domain of HER2 were synthesized colineary with the MVP T-helper epitope and stabilized by a disulfide pairing to mimic the native HER2 receptor. Antibodies elicited by MVF HER2(628-647) inhibited proliferation of human HER2 over-expressing breast cancer cells in vitro and caused their antibody-dependent cell-mediated cytotoxicity. Furthermore, immunization with MVF-HER2(628-647) prevented the spontaneous development of HER2 over-expressing mammary tumors in 83% of transgenic mice. Dakappagari et al. (2003) then identified further B cell epitopes that cross reacted with the cognate receptor, but only two of these B cell epitopes (316-339 and 485-503) induced tumor inhibitory antibodies. Vaccination with an appropriate combination of tumor inhibitory epitopes lead to an enhancement of the anti-tumor activities of the peptide antibodies mediated by much higher levels of receptor down-modulation and release of IFN-γ compared with antibodies elicited by single-epitope vaccines. In order to improve the affinity of the antibodies Dakappagari et al. (2005) designed a new HER2 construct (626-649, located downstream of the trastuzumab binding domain) in order to mimic the tertiary structure of the native epitope by introducing two disulfide bonds into the previously identified epitope. The authors stress that mimicking native protein structures is a prerequisite for designing effective humoral peptide vaccines. However, although the cyclized epitope led to an antibody population that showed improved binding to HER2, this did not translate into a more potent antiproliferative effect on breast cancer cells over-expressing HER2.

Jasinska et al. (2003) attempted to induce anti HER2 antibodies using a 7 putative B cell epitopes coupled to tenanus toxoid for immunization of BALB/c mice. The authors concluded from their animal experiments that immunization with the B-cell vaccine successfully induced a humoral immune response with anti-tumor activity in an animal model.

Riemer et al. (2004) reported the utility of the cysteine-constrained peptide phage display library for the identification of mimotopes capable of reacting with trastuzumab. Although, the mimotopes bear no direct homology to HER2, they have been shown to mimic the conformation of B-cell epitopes specifically recognized by trastuzumab. Immunization of Balb/c mice with one of their selected mimotopes conjugated to tetanus toxoid resulted in antibodies recognizing HER2 as well as causing internalization of the receptor in vitro. However, the antitumor activity and efficacy of these mimotope-vaccines has not been evaluated in an active immunization setting. These studies illustrate the potential clinical efficacy of establishing structural compatibility between peptide antibodies and native protein.

Whereas synthetic peptide mimotopes can easily be manufactured, are stable over long periods, do not include infectious material speaking for their safety, elicit a predetermined type of immune response while undesired epitopes are avoided and can be coupled to immunogenic carrier molecules (Partidos 2000; Riemer and Jensen-Jarolim 2007), it remains unclear whether peptide vaccines are sufficient to induce a therapeutic B-cell response in humans due to the necessity to break immunological tolerance and—especially with respect to conformational epitopes—whether linear or cyclized mimotopes can be fused to a support or CD4 helper epitopes while maintaining their activity with a required batch-to-batch consistency.

These and other vaccination strategies are reviewed and compared by Ladjemi et al. (2010). The authors conclude that clinical benefits of all anti-HER2 vaccination approaches remain questionable. While some problems/explanations for negative results are immanent to the clinical development of vaccines in general (deleterious impact of chemo- or radiotherapy prior to vaccination, extremely advanced stage of disease of chosen patient populations) one major difficulty is seen in the necessity of breaking immune tolerance against the HER2 antigen.

Together, despite the success with the anti HER2 monoclonal antibodies and the numerous vaccination approaches against HER2 there is still a high medical need to provide an improved, easy/cheap to manufacture, stable vaccine, which is not restricted to HLA haplotypes and is able to break tolerance against HER2 in humans.

The object is solved by providing parvoviral mutated structural proteins which comprise one or more mimotopes of HER2 capable of specifically binding to a monoclonal antibody directed against HER2. It was now possible to identify parvoviral mutated structural proteins which comprise such mimotopes from a library of high multiplicity of viruses that are able to induce high titers of antibodies in vivo (see Examples). The viral backbone is based on a structure of a virus that humans are familiar with (most humans are infected with the AAV2 which is not considered to have any known role in disease) and has previously been described as a suitable vaccination platform for linear B-cell epitopes (WO 2008/145401) including methods for identifying such parvovirus mutated structural proteins using selection by monoclonal antibodies.

Thus the present invention relates to a parvovirus mutated structural protein for inducing a B-cell response against human epidermal growth factor receptor (HER2) which comprises one or more mimotopes of HER2 capable of specifically binding to an antibody directed against HER2. The antibody to said mimotopes of HER2 which are capable to bind specifically might be selected from the group comprising trastuzumab (CAS number 180288-69-1), pertuzumab (CAS number 380610-27-5), MDX-H210 (CBNumber CB81342312), 2B1, C6.5xscFv(NM3E2), ertumaxomab (CAS number 509077-99-0) and FRP-5 derivates. In a preferred embodiment the antibody is trastuzumab or pertuzumab, especially trastuzumab.

The parvovirus mutated structural protein may also comprise several mimotopes binding to more than one antibodies directed against HER2, preferably antibodies selected from the group defined above.

A plurality of parvovirus mutated structural proteins may be capable of forming a capsomeric structure, capsid or virus-like particle. The one or more mimotopes of HER2 comprised in the parvovirus mutated structural protein are preferably arranged in the parvovirus mutated structural protein to be located on the surface of such capsomeric structure, capsid or virus-like particle. The location of the HER2 mimotopes on the surface of the capsomeric structure facilitates the presentation of the mimotopes to B-cell receptors. The surface is the exterior face of the capsomeric structure, capsid or virus-like particle. The surface is accessible to media surrounding the capsomeric structure, capsid or virus-like particle, particularly to B cells.

Manufacture of only one virus-like particle is cost efficient and they are stable and therefore suitable also for countries of the developing world.

The parvovirus from which the mutated structural protein is derived is selected from the group consisting of adeno-associated virus (AAV), bovine AAV (b-AAV), canine AAV (CAAV), canine parvovirus (CPV), mouse parvovirus, minute virus of mice (MVM), B19, H1, avian AAV (AAAV), feline panleukopenia virus (FPV) and goose parvovirus (GPV). The AAV may be AAV-1, AAV-2, AAV-3b, AAV-4, AAV-5, AAV-6, AAV-7, AAV-8, AAV-9, AAV-10, AAV-11 or AAV-12. AAV-2 is a specially preferred AAV.

The mutation comprised in the mutated structural protein may be an insertion and/or substitution of 4-50 (e.g. 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30, 41, 42, 43, 44, 45, 46, 47, 48, 49, or 50) amino acids, preferably 5-35 amino acids, especially 5-20 amino acids, preferably an insertion of 5-20 amino acids. The mutated structural protein may comprise several of said insertion and/or substitution(s). In a further embodiment the parvovirus mutated structural protein comprises at least one further mutation selected from a point mutation, an internal or terminal deletion, an insertion, preferably a second insertion, and a substitution. The one or more insertion and/or substitutions of 4-50 amino acids comprise the mimotope(s) of HER2. In specific embodiment the insertion(s) and/or substitution(s) are flanked by one or more linker sequences. Preferred sequences are those composed of or predominately comprising small amino acids, preferably Ala, Gly, Ser, Pro, and Cys, especially Ala upstream and two codons for Ala downstream of the randomized or partially randomized nucleic acid sequences, or an insertion of 2-5 glycin residues both, N or C-terminally of the insertion. Specific examples of such linkers are AAAGGG and GGGSG. Such additional amino acids may act as spacers to contribute to the proper accessibility of the inserted amino acids at the surface of the virions. In a further preferred embodiment the insertion comprises linker sequences which enable a circularization of the inserted peptide sequences in order to better present the insertion. Accordingly spacer sequences are selected to form Zinc-fingers (Zn-finger), well known in the art. Preferred Zn-finger motifs are $C_2H_2$, $C_4$, and $C_2HC$ including but not limited to motifs $CX_2CX_nC_2$, $CX_2CX_{10-30}CX_2C$, $CX_5HX_{10-30}CX_2C$, $CX_2CX_{10-30}CX_4H$ (Laity et al., 2001 and Gamsjaeger et al., 2006). An example of a preferred Zn-finger linker is:

$$X_{(3-5)} CXXCX_{(0-5)} (NNK)_n X_{(0-5)} CXXCX_{(3-5)}$$

(X=Gly or Ala, C=Cys; with each N being any nucleotide and K standing for G or T). Thus the random NNK sequence protrudes from the capsid surface. A highly preferred linker is also described in Example 1, wherein an $(NNK)_{15}$ insert (with N=A, G, C or T and K=G or T) with an upstream AAAGGG linker and a downstream GGGSG linker inserted after amino acid $N_{587}$ of the VP proteins is described.

The described insertion(s) is/are inserted into one or more positions selected from the group consisting of I-1, I-34, I-138, I-139, I-161, I-261, I-266, I-381, I-447, I-448, I-453, I-459, I-471, I-534, I-573, I-584, I-587, I-588, I-591, I-657, I-664, I-713 and I-716, preferably I-453 and I-587, especially I-587. In a preferred embodiment the insertion(s) is/are inserted into I-453 and/or I-587, more preferably into I-453 and/or I-587 of AAV-1, AAV-2 or AAV-6, especially into I-587 of AAV-2. The used nomenclature I-### refers to the insertion site with ### naming the amino acid number relative to the VP1 protein of AAV2, however meaning that the insertion may be located directly N- or C-terminal, preferably directly C-terminal of one amino acid in the sequence of 5 amino acids N- or C-terminal of the given amino acid, preferably 3, more preferably 2, especially 1 amino acid(s) N- or C-terminal of the given amino acid. For parvoviruses other than AAV2 the corresponding insertion sites can be identified by performing an amino acid alignment or by comparison of the capsid structures, if available. Such alignment has been performed for the parvoviruses AAV1, AAV-6, AAV2, AAV-3b, AAV-7, AAV-8, AAV10, AAV-4, AAV11, b-AAV, AAV-5, GPV, B19, MVM, FPV and CPV (see e.g. FIG. 1 of WO 2008/145401).

In a further embodiment of the invention, the parvovirus mutated structural protein comprises at least one further mutation selected from a point mutation, an internal or terminal deletion, an insertion, preferably a second insertion, and a substitution at a different position. Such further mutation can be used to compose more complex mimotopes, to modify certain properties of the virion, e.g. it can be use to modify its natural antigenicity (e.g. WO 01/05990), to modify its chromatographic properties (e.g. WO 01/05991), etc. Preferably, the further (second) insertion is internally or a N- or C-terminal fusion, whereas the further insertion has a length of 4 to 40, preferably of 5 to 30, most preferably of 7 to 20 amino acids. In one specific embodiment the insertion is a tag useful for binding to a ligand. Such tags are well known in the art, examples for such are His tag, GST tag, Protein A tag, Biotin tag, Strep tag, Calmodulin-binding peptide tag, Fc tag, Flag tag or HA tag.

In a further embodiment of the invention, the parvovirus mutated structural protein described herein is a fusion protein additionally comprising a second protein or peptide domain. The second protein may be any protein, e.g. those described above.

In a further embodiment the amino acid sequence of the one or more mimotopes comprised in the parvovirus mutated structural protein described herein is not present in a wild type parvoviral structural protein, preferably wherein the wild type parvoviral structural protein is not capable of specifically binding to Trastuzumab. The sequences of wild type parvoviral structural proteins are known in the art and available from well-known public data bases.

In still another preferred embodiment of the present invention, the at least one HER2 mimotope comprised in the parvovirus mutated structural protein described herein comprises at least one of amino acid sequences of (SEQ ID NO: 66)
(W/H/Y/V)xxGx(A/L/V/C/E)xG(S/M/D/E/V/N/G/R/T)

preferably (SEQ ID NO: 67)
WxxGx(A/V/L)xG(S/T/M/D/E)

more preferably (SEQ ID NO: 68)
Wx(S/T/K/R/M/L/A/V)Gx(A/V)xG(S/M/D)

more preferably (SEQ ID NO: 69)
Wx(K/R/E/S/T/F)G(L/M/T/V)A(A/V/L/E/D)G(S/T/D/E/M)

more preferably (SEQ ID NO: 70)
(S/T/G)(S/T/R/Q/H/L)Wx(K/R/S/E/F)G(L/M/T/V)A
(A/V/L/E)G(S/D/M)(G/V/L/I/S/C/F)

especially (DMD02 shortened-SEQ ID NO: 100)
TRWQKGLALGSG (DMD18 shortened-SEQ ID NO: 101)
GRWSEGTALGSS (DDDD63 shortened-SEQ ID NO: 102)
GQWARGLAVGSC (DDD29 shortened-SEQ ID NO: 103)
GTWERGVAAGDI (DMD11 shortened-SEQ ID NO: 104)
TLWHRGLAAGDV (DMM44 shortened-SEQ ID NO: 105)
SWASGMAVGSV (DDM52 shortened-SEQ ID NO: 106)
WAFGLALGSL (DDD25 shortened-SEQ ID NO: 107)
QWLEGLAEGMV (DMD04 shortened-SEQ ID NO: 108)
SHWVSGLAEGSF or preferably (SEQ ID NO: 71)
(S/T/L/Q)Wx(M/A/L/V)G(T/A/S/M)A(Q/A/V/H/K/R)
G(S/T/D/E)

more preferably (SEQ ID NO: 72)
(S/T/G)(S/T/Q)W(K/R/A)(M/A/L)G(T/A/M)A(Q/A/V/R)
G(S/D)(G/F/S)(Q/K/V)(D/G)

especially (DDD22 shortened-SEQ ID NO: 109)
WKMGTAQGSGQD

-continued
(DDDD65 shortened-SEQ ID NO: 110)
WKMGMAQGSGQD (DDM47 shortened-SEQ ID NO: 111)
GSWKLGTARGSG (DMD05 shortened-SEQ ID NO: 112)
SSWAAGTAAGDFKG (DDD55 shortened-SEQ ID NO: 113)
CQWRAGTAVGSSVG or preferably (SEQ ID NO: 73)
Wx(S/T/A/L/V)Gx(A/V)(E/D/A/V/H/K/R)
G(S/T/D/E/N/G/V), more preferably (SEQ ID NO: 74)
(S/R/V)xWx(S/L/V)G(Q/R/N/M/W/D)(A/V/S)(E/D/V/H)
G(S/D/E/N/V)(E/D/S/R), especially (DMD03 shortened-SEQ ID NO: 114)
RTWQSGMADGEE (DMD07 shortened-SEQ ID NO: 115)
SLWLLGRADGVS (DDD62 shortened-SEQ ID NO: 116)
WMSGQSDGSS (DDD20 shortened-SEQ ID NO: 117)
VAWSSGQAHGSR (DDD54 shortened-SEQ ID NO: 118)
SAWLLGNVEGSE (DDD57 shortened-SEQ ID NO: 119)
SGWSVGWADGDD (DDD21 shortened-SEQ ID NO: 120)
WDSGDAVGNE or preferably (SEQ ID NO: 76)
(W/H/Y/V)x(S/T/A/V/L)Gx(A/V/L/C/E)(E/D/K/R/H)
G(S/T/G/V/R)

more preferably (SEQ ID NO: 77)
(L/R)x(W/H/Y/V)x(S/T/V)G(K/R/N/E/L)(A/V/L/C/E)
(E/D/K/R)G(S/T/G/R)xx(L/R/P/Q/W).

especially (DDD28 shortened-SEQ ID NO: 121)
LKWYSGELEGSKEL (DMD06 shortened-SEQ ID NO: 122)
LSHTSGRVEGSVSL -continued (DDD23 shortened—SEQ ID NO: 123)
GWNSGKVDGGAGR (DDD32 shortened—SEQ ID NO: 124)
YFSGKAEGREAP (DMM45 shortened—SEQ ID NO: 125)
VTGNCKGSRQQ (DMD01 shortened—SEQ ID NO: 126)
RLVPVGLERGTVDW or (SEQ ID NO: 79)
(W/F/K)x(N/K/H/E/S/C)xxx(S/G/I/V)(S/T/K/R/W)
(G/S/E/K), preferably (SEQ ID NO: 80)
(W/F)x(N/H/K/E)xxx(S/G/I/V)(S/T/K/R)(G/K)
(G/E/S/H)x(R/K/L/G), especially (DDM53 shortened—SEQ ID NO: 127)
WGEPYSGKGSHG (DMD13 shortened—SEQ ID NO: 128)
WGNCPLSSGGPK (DMM36 shortened—SEQ ID NO: 129)
WRHKHIVTKGGL (DMM46 shortened—SEQ ID NO: 130)
WAHGEDITGHSL (DMD17 shortened—SEQ ID NO: 131)
FPKSQVSRGEMR or preferably (SEQ ID NO: 81)
(F/K)xx(S/D)xxS(R/W)(G/S/E)(G/E/P)x(R/K)

especially (DMD17 shortened—SEQ ID NO: 131)
FPKSQVSRGEMR (DMM38 shortened—SEQ ID NO: 132)
KNCDRLSWSGAR (DMM41 shortened—SEQ ID NO: 133)
FLSDKYSREPHK or (SEQ ID NO: 83)
(R/D)(S/T/F/L)x(E/D/S/C)xxG(G/C/S/K)

more preferably (SEQ ID NO: 84)
RSx(E/D)xxG(G/C)xx(E/D/R)(V/A/L/R)

especially (DMD09 shortened—SEQ ID NO: 134)
RSFEKFGGMKER (DDM50 shortened—SEQ ID NO: 135)
RSNDVLGCKLRV or preferably (SEQ ID NO: 85)
(R/D)(S/T/F/L)(S/T/L)(S/C)xxG(G/C/S/K)(P/E/I)
(M/N/C/Y)(E/D/V/S/M)(V/A/L/H)

especially (DMD15 shortened—SEQ ID NO: 136)
DSTSLAGGPYEA (DMM43 shortened—SEQ ID NO: 137)
RLSSAQGCINMV (DMM42 shortened—SEQ ID NO: 138)
RTLCGTGSEMVL (DDM49 shortened—SEQ ID NO: 139)
RFSCAVGKECSH (DMD16 shortened—SEQ ID NO: 140)
LSRCGKPMDV or (SEQ ID NO: 87)
(K/R/M/G/D)x(W/Y/S/T/F/I)x(R/N/S/T/L)(K/R/E/D/L)

preferably (SEQ ID NO: 88)
(D/G)x(Y/Q/T/G)(E/W/Q/L)x(H/R/S/C)(K/R)(K/H/S/T)
(S/T/F/I)(L/V/Q)(R/N/S/T/L)(K/R/E/L)(E/A/G)

especially (DMM36 shortened—SEQ ID NO: 141)
DVTWRHKHIVTKG (DMM37 shortened—SEQ ID NO: 142)
GGYEVRKHFQSRE (DDD26 shortened—SEQ ID NO: 143)
DPYESSRSTLLRA (DMM35 shortened—SEQ ID NO: 144)
DVGQGRRKSLNLE (DDM48 shortened—SEQ ID NO: 145)
MQLICRTSLREE or preferably (SEQ ID NO: 89)
(V/L/I)(S/V/I)(K/R/M/G/D)(K/H/N/P)(W/Y)x
(R/N)(E/D)(E/C/P)

especially

```
                       (DDD19 shortened-SEQ ID NO: 146)
VVMNWMREE (DDDD64 shortened-SEQ ID NO: 147)
VIGPYEREC (DMM41 shortened-SEQ ID NO: 148)
LSDKYSREP
``` or

```
                                            (SEQ ID NO: 91)
(G/A/S)x(A/V/I/R/E/Q)(K/S/T/A/G/E)x(W/L)

(P/D/E/A/G/S)xxx(E/S/L/K/A)
``` preferably

```
                                            (SEQ ID NO: 92)
(G/A)x(A/V/R)(K/S)x(W/L)(P/A)(N/E)CG(S/L)x(E/Q)
``` especially

```
                       (DMD08 shortened-SEQ ID NO: 149)
GRAKNLPNCGSGQ (DMD14 shortened-SEQ ID NO: 150)
GSRSMWAECGLDE
``` or preferably

```
                                            (SEQ ID NO: 93)
(G/S)x(A/V/E/Q)(A/K/E)xW(P/D/E)(I/E/R/S/T)

(I/V/K)(R/A/G)(E/L)x(E/Q/L/M)
``` especially

```
                       (DMM34 shortened-SEQ ID NO: 151)
GVVKAWDSIRLVE (DDD27 shortened-SEQ ID NO: 152)
GDEEMWPIVRELQ (DDD31 shortened-SEQ ID NO: 153)
GAAAQWPEVREYL (DMM40 shortened-SEQ ID NO: 154)
SVQKKWERKAESM
``` or preferably

```
                                            (SEQ ID NO: 94)
(V/Q/E)(E/G/T/V)(K/L/V/H)W(P/S/D/E/G)

(I/A/V/E/R/S/T)x(K/V/T/D)(E/K/A)(V/S/T/P/E)

(S/V/W)
``` especially

```
                       (DMM39 shortened-SEQ ID NO: 155)
VEHWSRSKKSS (DDD24 shortened-SEQ ID NO: 156)
VGVWPVMVETV
```

```
                       (DDD30 shortened-SEQ ID NO: 157)
QTKWPIATEVW (DDD56 shortened-SEQ ID NO: 158)
EVLWGEMDAPW
``` or preferably

```
                                            (SEQ ID NO: 95)
(V/I)(S/T)(L/K)W(D/E)xGLAE
``` especially

```
                       (DDD60 shortened-SEQ ID NO: 159)
VTLWETGLAE (DDD61 shortened-SEQ ID NO: 160)
ISKWDAGLAE
``` or

```
                                            (SEQ ID NO: 97)
(E/D/V/A)(P/Q/N/E/RL/C)(I/A/V/S/T)(S/T/A)(A/T)

(H/K/R/Q)(S/K/G)(R/S/C)(Y/A/I/V)xx(V/A/M)
``` preferably

```
                                            (SEQ ID NO: 98)
(E/V)(P/Q)(L/C)(I/A/V)(S/T/A)A(H/K/R)K(R/S)YxxV
``` especially

```
                       (DMD10 shortened-SEQ ID NO: 161)
EPCITAHKSYMRV (DMM33 shortened-SEQ ID NO: 162)
VQLASAKKRYLGV
``` or preferably

```
                                            (SEQ ID NO: 99)
(E/V)(E/R/Q)(L/C)(V/S)(S/T/A)(A/T)(R/Q)(S/K/G)

(R/S/C)(A/I/V)xx(V/M)

(DDD58 shortened-SEQ ID NO: 163)
EELVATRSRAGGM (DMM43 shortened 2-SEQ ID NO: 164)
VRLSSAQGCINMV
``` or

```
                       (DMD12 shortened-SEQ ID NO: 165)
SESGVFVLQSCAWEY (DDD59 shortened-SEQ ID NO: 166)
SCLARVHCDMPREWE
``` or especially a mimotope selected from the group consisting of

```
                                            (SEQ ID NO: 126)
RLVPVGLERGTVDW, (SEQ ID NO: 100)
TRWQKGLALGSG,
```

```
                                (SEQ ID NO: 108)
    SHWVSGLAEGSF, (SEQ ID NO: 122)
    LSHTSGRVEGSVSL,
``` or any of such sequences having one or two amino acid exchange(s), preferably one or two conservative amino acid exchange(s).

In another aspect the present invention relates to a composition for inducing a B-cell response comprising:
a) a support capable of presenting peptides in a repetitive array; and
b) at least three peptides, identical and/or different, each having an amino acid sequence independently selected from the amino acid sequence as defined afore, particularly sequences of SEQ ID NO: 66 to 166) and in the Examples, the peptides being joined to the support so as to form a HER2 mimotope-presenting support.

The support capable of presenting peptides in a repetitive array may be selected from the group consisting of a bead, a lipid membrane, a protein or polypeptide, a carbohydrate, especially a sugar, a polymer or an inorganic carrier. Said bead may be selected from a polyacrylamide bead, an agarose bead, a polystyrene bead, a magnetic bead, a latex particle or a carbohydrate assembly (e.g., oligosaccaride-based bead or assembly, e.g. wherein the carbohydrate is cellulose, starch, glycogen, chitosane or aminated sepharose). The afore described lipid membrane may be selected from a lipid assembly and a liposome. The protein capable of presenting peptides in a repetitive array may be selected from a protein assembly, preferably a protein assembly of a structural protein of a virus or phage, especially a capsid, a virus-like particle or a virus, a polymer, preferably poly-L-lysine or poly-D, L-alanine, KLH (Keyhole limpet hemocyanin), andLPH (Hemocyanin from *Limulus polyphemus* hemolymph). The afore described inorganic carrier may be selected from silica material (e.g. silica gel, zeolite, diatomaceous earth or aminated glass) with the HER2 mimotopes covalently linked through a hydroxy, carboxy or amino group and a reactive group on the carrier.

In a further aspect, the present invention relates to a multimeric structure comprising parvovirus mutated structural proteins of as described above, preferably wherein the structure is an aggregate of at least 5, preferably at least 10, more preferably at least 30, most preferably at least 60 mutated structural proteins (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30, 41, 42, 43, 44, 45, 46, 47, 48, 49, 50, 51, 52, 53, 54, 55, 56, 57, 58, 59, 60 or more). This multimeric structure may be a capsomeric structure, capsomer, a capsid, a virus-like particle or a virus. In a preferred embodiment, the virus like particle comprises only parvovirus mutated structural proteins derived from VP3.

In a preferred embodiment, the multimeric structure comprises one or more HER2 mimotopes, preferably one or more HER2 mimotopes as defined above, is/are located on the surface of the multimeric structure. The location of the HER2 mimotopes on the surface of the capsomeric structure facilitates the presentation of the mimotopes to B-cell receptors. The term "surface" is defined as described above.

In a one embodiment, the HER2 mimotopes present on the surface of one multimeric structure as described herein is 10-500 angstroms, preferably 50-300 angstroms, especially 80 to 120 angstroms. The distance is to be determined as the length of the shortest line on the surface of the virus joining two mimotopes.

The present invention also relates to nucleic acid coding for a parvovirus mutated structural protein as described above, preferably coding for an amino acid sequences disclosed herein. Said nucleic acid of the invention may be comprised in an expression cassette, construct, or vector. A construct, typically a plasmid, is generally a nucleic acid comprising the nucleic acid of the invention and additional sequences such as polycloning sites, origin of replication, selection marker genes etc. An expression cassette is generally a construct that, once it is inside a cell, is able to produce the protein encoded by the nucleic acid of the invention by the cellular transcription and translation machinery. The expression construct is engineered to contain regulatory sequences that act as enhancer or promoter regions and lead to efficient transcription of the nucleic acid of the invention. It further usually comprises a poly(A)-site that is later polyadenylated which is important for nuclear export, translation and stabilization of the mRNA. Vectors are constructs that are used to introduce the nucleic acid of the invention into cells. Dependent on the cells to be transfected they are constructed according to standard skills of the artisan.

Accordingly the invention also relates to a cell comprising the nucleic acid described herein. The cell may be a bacterium, a yeast cell, an insect cell or a mammalian cell. The selected cell may depend on the nature and properties of mutated structural protein encoded by the nucleic acid and the use of the mutated structural protein.

The structural protein described according to the invention may be prepared according to a method comprising the steps of:
a) expressing the nucleic acid coding for the parvovirus mutated structural protein by cultivating a cell as described above under suitable conditions, and
b) isolating the expressed parvovirus mutated structural protein of step a).

In a preferred embodiment, the structural protein described according to the invention is co-expressed with the assembly activating protein (AAP) (as described in (Sonntag et al., 2010) and in the examples herein. The sequence encoding AAP can be provided either in cis or in trans to assemble capsids consisting of the structural protein described herein.

The structural protein according to the invention can be used in a medicament comprising at least one parvovirus mutated structural protein as described herein, a composition as described herein, a nucleic acid as described herein and/or at least one multimeric structure as described herein, and at least one suitable excipient, carrier and/or stabilizer. In a specific embodiment the medicament is a medicament for use in a method for treating or preventing a HER2-related disease, preferably cancer, especially breast cancer.

Furthermore the invention relates to a vaccine comprising at least one parvovirus mutated structural protein as described herein, a composition as described herein, a nucleic acid as described herein and/or at least one multimeric structure as described herein, and at least one suitable adjuvant, excipient, carrier and/or stabilizer. A vaccine is a composition, preferably a suspension, of dead, attenuated, or otherwise modified microorganisms for inoculation to produce an immune response to a disease by stimulating the production of antibodies. The excipient, carrier and/or stabilizer useful in this invention are conventional and may include buffers, stabilizers, diluents, preservatives, and solubilizers. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate The adjuvant comprised in said vaccine may be selected from the group consisting of mineral oil-based adjuvants, preferably Freund's complete or incomplete adjuvant, Montanide incomplete Seppic adjuvants, preferably ISA, oil in water emulsion adjuvants, preferably Ribi adjuvant system, syntax adjuvant formulation containing muramyl dipeptide, and aluminum salt adjuvants.

In a preferred embodiment the adjuvant is a mineral oil-based adjuvant, especially ISA206 (SEPPIC, Paris, France) or ISA51 (SEPPIC, Paris, France), or selected from the group consisting of CpG, Imidazoquinolines, MPL, MDP, MALP, flagellin, LPS, LTA, cholera toxin, a cholera toxin derivative, HSP60, HSP70, HSP90, saponins, QS21, ISCOMs, CFA, SAF, MF59, adamantanes, aluminum hydroxide, aluminum phosphate and a cytokine.

In one embodiment, the composition and/or vaccine according to the invention comprises a combination of more than one, preferably two, adjuvants.

In a further aspect the invention relates to a method of inducing a B-cell response against HER2 comprising the step of administering parvovirus mutated structural protein as described herein, a composition as described herein, a nucleic acid as described herein, multimeric structure as described herein, the medicament as described herein or the vaccine as described herein, in an effective dose to a mammal, preferably human.

In a further aspect the invention relates to a method of treating a HER2-related disease comprising the step of administering the Parvovirus mutated structural protein as described herein, a composition as described herein, a multimeric structure as described herein, a nucleic acid as described herein, a medicament, particularly a vaccine, in an effective dose to a mammal, preferably human.

In the method of inducing a B-cell response described above or the method of treating a HER2-related disease described above, the medicament according to the invention or the vaccine according to the invention is administered parenterally, preferably intra muscularly, subcutaneously, intranasally, intra-lymphnodularily, intradermally, intraperitoneally or intravenously, especially intramucularly.

In a specific embodiment of the methods described above, parvovirus mutated structural protein as described herein, a composition as described herein, a nucleic acid as described herein, multimeric structure as described herein, the medicament as described herein or the vaccine as described herein is administered to a human multiple times, such as one, or two, or three, or four, our five, or more than five times.

In a specific embodiment of the methods described above, the HER2-related disease is cancer, particularly breast, ovarian, bladder, salivary gland, endometrial, pancreatic and non-small-cell lung cancer, especially breast cancer.

The compositions described herein in the context of the medicaments or vaccines of the present invention may be used as a medicament or vaccine and/or in the treatments of the diseases described herein. The following definitions explain how the defined terms are to be interpreted in the context of the products, methods and uses of the present invention.

"aa" means amino acid, "aas" means amino acids. Individual amino acids are generally given in the one letter code with x standing for any natural occurring amino acid.

A "structural protein" means a protein that is part of the capsid of the virus. For parvoviruses the structural proteins are generally referred to as VP-1, VP-2 and/or VP-3.

A "mutated structural protein" means a structural protein that has at least one mutation in comparison to the respective structural protein of the wild-type virus.

A "parvovirus" means a member of the family of Parvoviridae containing several genera divided between 2 sub-families Parvovirinae (Parvovirus, Erythrovirus, Dependovirus, Amdovirus and Bocavirus) and Densovirinae (Densovirus, Iteravirus, Brevidensovirus, Pefudensovirus and Contravirus) (Fields: Virology, fourth edition 2001, Volume 2, chapters 69 and 70, Lippincott Williams Wilkins, Philadelphia; http://virus.Stanford,edu/parvo/parvovirus.html http://www.ncbi.nlm.nih.gov/ICTVdb/lctv/fs_parvo.htm#SubFamily1). Preferred parvoviruses are members of the genus Parvovirus, such as AAV1, AAV2, AAV-3b, AAV-4, AAV-5, AAV-6, AAV-7, AAV-8, AAV-9, AAV10, AAV11, AAV12, bovine AAV (b-AAV), canine AAV (CAAV), canine parvovirus (CPV), mouse parvovirus, minute virus of mice (MVM), B19, H1, avian AAV (AAAV), feline panleukopenia virus (FPV) and goose parvovirus (GPV).

Preferred parvoviruses are adeno-associated virus (AAV), Bovine AAV (b-AAV), canine AAV (CAAV), canine parvovirus (CPV), minute virus of mice (MVM), B19, H1, AAAV, feline panleukopenia virus (FPV) and goose parvovirus (GPV). Especially preferred are AAV1, AAV2, AAV-3b, AAV-4, AAV-5, AAV-6, AAV-7, AAV-8, AAV-9, AAV10, AAV11 or AAV12, especially AAV2.

"Heterologous" in the context of the present invention means a peptide sequence, e. g. an epitope, which is not present on the parvovirus wild type viral capsid and/or structural protein.

A "mimotope" is an epitope mimicking the B-cell epitope or antigen, here HER2, whereas mimicking means that the mimotope has no aa sequence homology (i.e. less than 50% of aa identity) to the B-cell epitope, but only structural similarity. This means that the mimotope is a molecular mimicry of a corresponding B-cell epitope, wherein the electron cloud of a B-cell epitope specifically recognized by a B cell or immune globulin is built from aas which have no aa sequence homology to such B-cell epitope, but are also specifically recognized by such B cell or immune globulin. Typically, small peptides from 6-38 amino acids resemble such B-cell epitopes. However, in the context of this invention aas of the structural protein may contribute to such electron cloud, which in this case may be built in part from the mutation and in part from aas of the structural protein which are in the three dimensional structure in close proximity to the mutation. The B-cell epitope of the antigen, here HER2, may be itself a linear epitope or a non-linear structural, discontinuous epitope composed of several aas derived from different regions of the linear sequence of the antigen located in close neighborhood due to the overall tertiary structure of the antigen.

"AAVLP" or "AAV like particles" shall mean virus-like particles comprising parvoviral or preferably AAV structural proteins but no viral genome. In a preferred embodiment such AAVLPs are essentially consisting of VP3 as defined in Sonntag et al. (2010a, and b). The capsomeric structure is comprised of viral capsid proteins that self-assemble to form an organized structure. Such viral capsid assemblies are referred to as "virus-like particle," or VLPs. The term "virus-like particle" or "capsomeric structure" is used to refer to an organized structure comprising self-assembling ordered arrays of capsid proteins that do not include a viral genome. The VLP may be a "chimeric virus-like particle". The term "chimeric VLP" refers to a VLP where the mimotope is joined to or inserted into the viral capsid protein (or its homolog) by genetic engineering (e.g., creation of mimotope/capsid protein fusion). The term "capsid" denotes the protein shell of a virus that encloses the nucleic acid. The capsid including the nucleic acid is referred to as virus.

An "insertion" of aa/aas is generally speaking of an insertion of at least one heterologous aa into the sequence of—for this invention—a parvovirus structural protein. The inserted aa/aas can simply be inserted between two given amino acids of the parvovirus structural protein. An insertion of aa/aas can also go along with a deletion of given aa/aas of the parvovirus structural protein at the site of insertion, leading to a complete substitution (e. g. 10 given aas are substituted by 10 or more inserted aas) or partial substitution (e. g. 10 given aas are substituted by 8 inserted aas) of aas of the parvovirus structural protein.

With respect to the nomenclature of suitable positions for insertions into the parvoviral structural protein (e.g. I-587) it is referred to Büning et al. (2008), specifically page 21 to 26. Briefly, I-### refers to the insertion site with ### naming the amino acid number relative to the VP1 protein of AAV2, however meaning that the insertion may be located directly N- or C-terminal, preferably directly C-terminal of one amino acid in the sequence of 5 amino acids N- or C-terminal of the given amino acid, preferably 3, more preferably 2, especially 1 amino acid(s) N- or C-terminal of the given amino acid. For parvoviruses other than AAV2 it is referred to Büning et al. (2008), specifically page 21 to 26.

The term "specifically binding" or "specifically bound" means that two molecules A and B, preferably proteins, bind to each other thereby generating complex AB with an affinity ($K_D=k_{off}/k_{on}$) of at least $K_D=1\times10^{-5}$ mol/l, preferably $1\times10^{-7}$ mol/l, more preferably $1\times10^{-8}$ mol/l, especially $1\times10^{-9}$ mol/l. In the context of the present invention the mimotopes of HER2 are capable of specifically binding to an antibody directed against HER2, particularly to trastuzumab, pertuzumab, MDX-H210, 2B1, C6.5xscFv (NM3E2), ertumaxomab and FRP-5 derivates, more particularly to trastuzumab or pertuzumab, especially trastuzumab, with an of at least $K_D=1\times10^{-5}$ mol/1, preferably $1\times10^{-7}$ mol/1, more preferably $1\times10^{-8}$ mol/l, especially $1\times10^{-9}$ mol/l.

The term "conservative amino acid exchange" means that one aa is exchanged by one other aa with similar chemical properties, i.e. aa exchanges within the following groups:
aliphatic aas G, A, V, L and I;
aromatic aas F, Y and W;
aas C and M having an sulfur containing side chain;
aas S and T having an hydroxyl group;
basic aas L, R and H; and
acidic aas D, E, N and Q.

The term "plurality", particularly with respect to structural proteins or Parvovirus mutated structural proteins, means any number larger than 3, preferably at least 5, preferably at least 10, more preferably at least 30, most preferably at least 60.

The term "more" as used in the feature "one or more", particularly with respect to the mimotopes of HER2, means any number larger than 2, such as 2, 3, 4, 5, 6, 7, 8, 9, or 10, preferably at least 3, preferably at least 5, more preferably at least 7, most preferably at least 10.

The term "inducing a B-cell response" means that upon vaccination of a mammal with an antigen, in the context of this invention with a parvovirus mutated structural protein comprising a HER2 mimotope, B cells are induces to produce immune globulins which are capable of specifically binding the vaccination antigen, in this case the HER2 mimotope and/or the respective HER2 epitope. For example, upon vaccination of mice immune sera can be collected. Such immune sera can either directly be used in e.g. an ELISA in order to determine specific binding to recombinant HER2. Alternatively, immune sera can be purified with protein G sepharose and used in such ELISA analysis. For example, an $OD_{450}$ under conditions of the examples greater than 0.1 with less than half of the $OD_{450}$ for the negative control with a different IgG monoclonal antibody resembles specific binding.

Preferred anti-HER2 antibodies are trastuzumab, pertuzumab, MDX-H210, 2B1, C6.5xscFv(NM3E2), ertumaxomab and FRP-5 derivates, especially trastuzumab or pertuzumab, especially trastuzumab.

Preferred tumor indications are breast, ovarian, bladder, salivary gland, endometreial, pancreatic and non-small-cell lung cancer, especially breast cancer.

In another preferred embodiment, and of the above HER2 mimotopes might be combined with a HER2 mimotope sequence obtained from a library with a linear HER2 epitope sequence, e.g. those published in (Dakappagari et al. 2005). The combination might be in one mutated structural protein or one multimeric structure or in different mutated structural proteins or different multimeric structures. This combination should be advantageous, as it seems that vaccines with more than one epitope have stronger efficacy.

Another preferred embodiment for generating vaccines with more than one HER2 mimotopes and/or epitopes is the coexpression of genes each encoding for a structural protein with one mimotope/epitope insert thereby generating mosaic multimeric structures, e.g. mosaic virus-like particles.

FIGURES

FIG. 1: Image of analytical agarose gel (1%) of PCR products from AAV 2 library screen. Line 1: marker, line 2: 5 μl of 20 μl PCR product, line 3: 1 μl of 20 μl PCR product, line 4: negative control.

FIG. 2: Sandwich ELISA of HER2 mimotope AAVs DMD01 to DMD06 from cell lysates. AAVs were immobilized by A20 mAb to ELISA plate and detected by trastuzumab (100 μl of 10.0 μg/ml) or an HER2 unspecific IgG mAb. As negative control AAV containing a HER2 unspecific epitope was used. $OD_{450}$ after subtraction of the negative value is shown.

FIG. 3: Indirect ELISA of HER2 mimotope AAVs DMD01 to DMD07, DMD15, DMD18, DDD19, DDD21, DDD30 and DDD31 and wild type AAV. AAV were bound to the ELISA plate and trastuzumab or a different humanized IgG-1 monoclonal antibody as a negative control added.

FIG. 4: Sandwich ELISA of HER2 mimotope AAVs DMD01 to DMD07, DMD11, DMD15, DMD18, DDD19, DDD21, DDD30, DDD31, DMM44 and wild type AAV.

A20 monoclonal antibodies coated ELISA plates were used to immobilize the AAV particles and subsequently trastuzumab (100 µl of a 10 µg/ml dilution in PBS/0.01% Tween-20) or a different humanized IgG-1 monoclonal antibody was added as a negative control.

Figure 5:
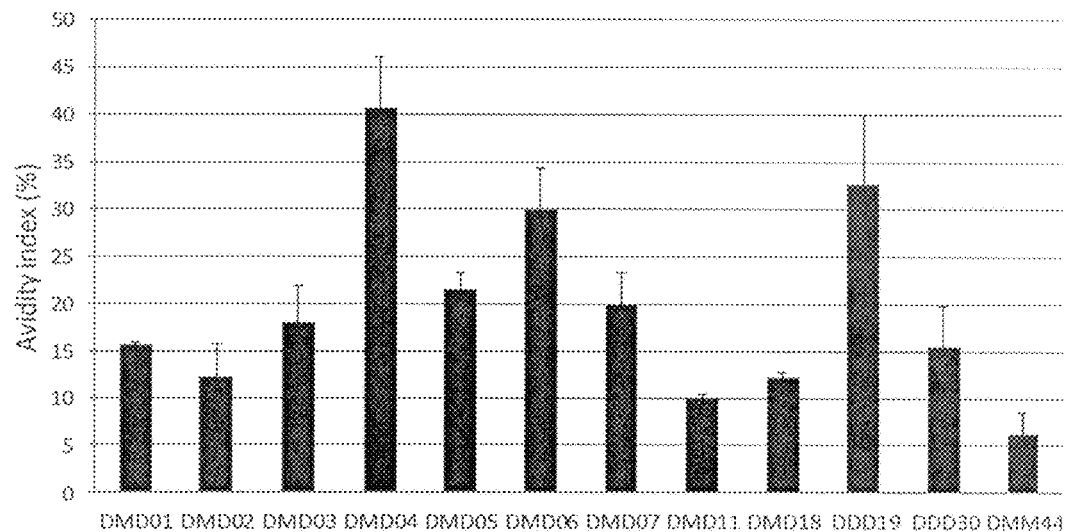

FIG. 5: Sandwich ELISA of HER2 mimotope AAVs DMD01 to DMD07, DMD11, DMD18, DDD19, DDD30 and DMM44. AAVs were immobilized to ELISA plate in duplets and detected by trastuzumab at two different, pre-determined, optimal concentrations with or without washing under chaotropic conditions (5M urea). Avidity indices in % were calculated as a ration between $OD_{450}$ with or without the chaotropic wash step.

Figure 6:
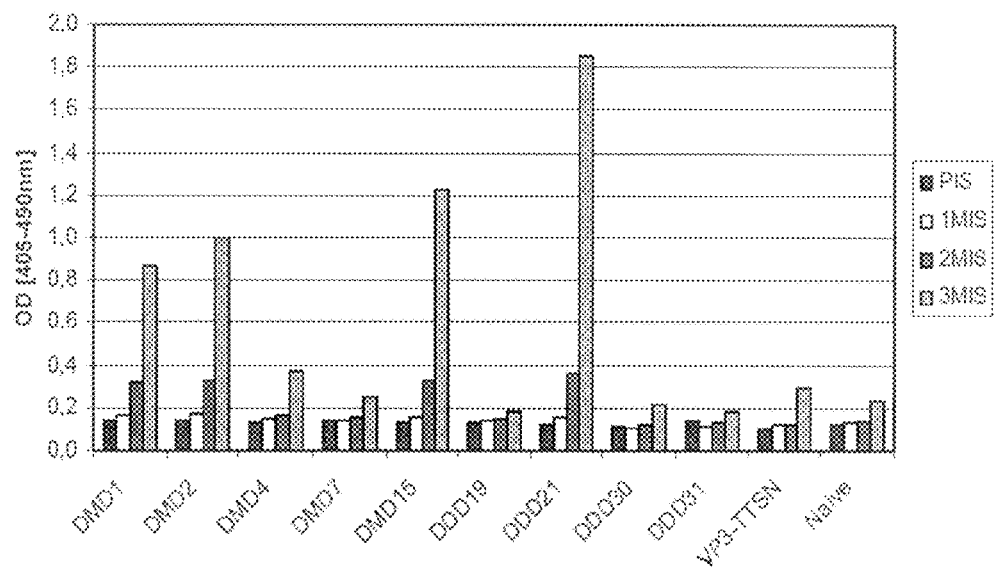

FIG. 6: ELISA for screening of sera of immunized mice (PIS=pre immune sera, MIS=mouse immune sera after respective immunization/boost) for specific IgG1 antibodies against HER2. Mice were immunized with indicated AAV clones. VP3-TTSN, an AAV containing an unrelated mimotope insert served as negative control.

Figure 7:
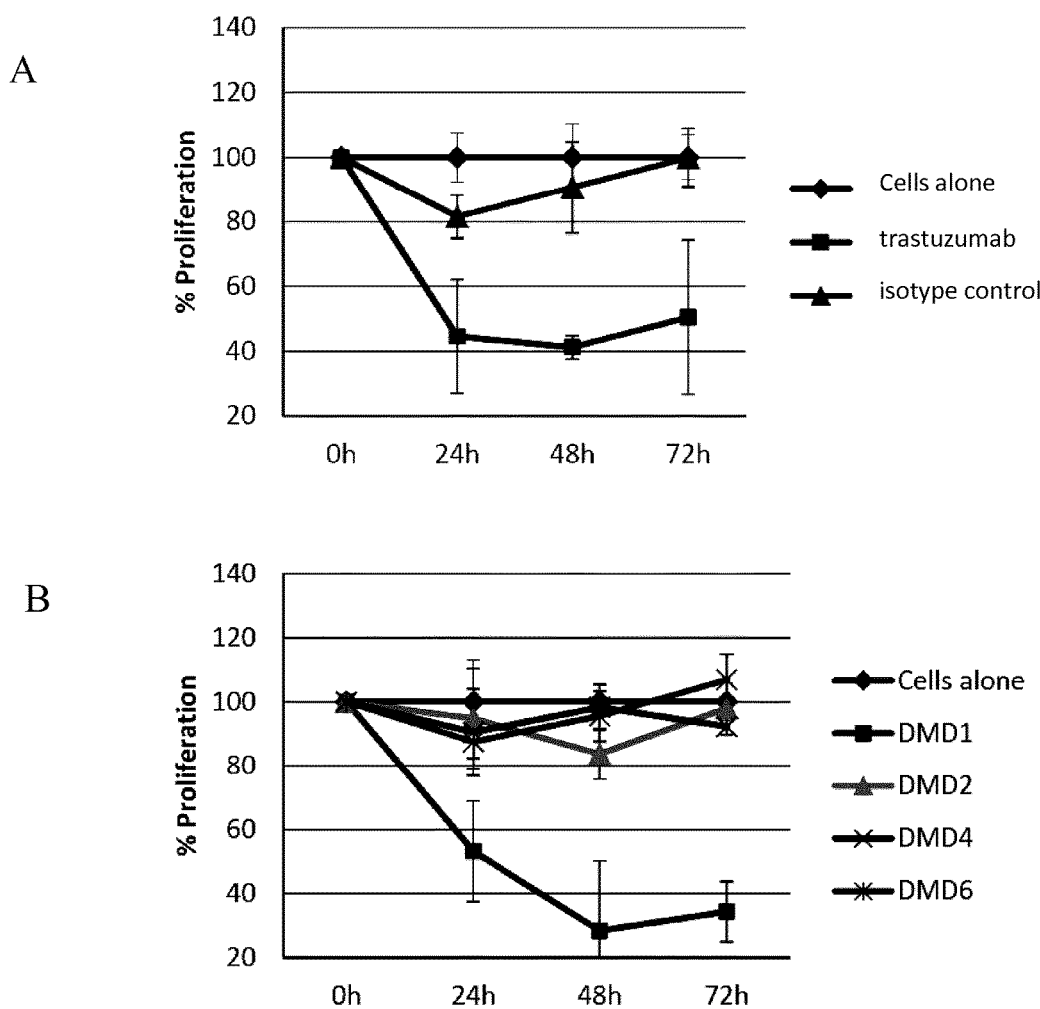

FIG. 7: EZ4U cell proliferation assay for mBT474 human breast cancer cells (passaged once through SCID mice) after incubation with (A) trastuzumab, an isotype control or (B) DMD01, DMD02, DMD04 or DMD06 compared each to untreated cells.

Figure 8A:
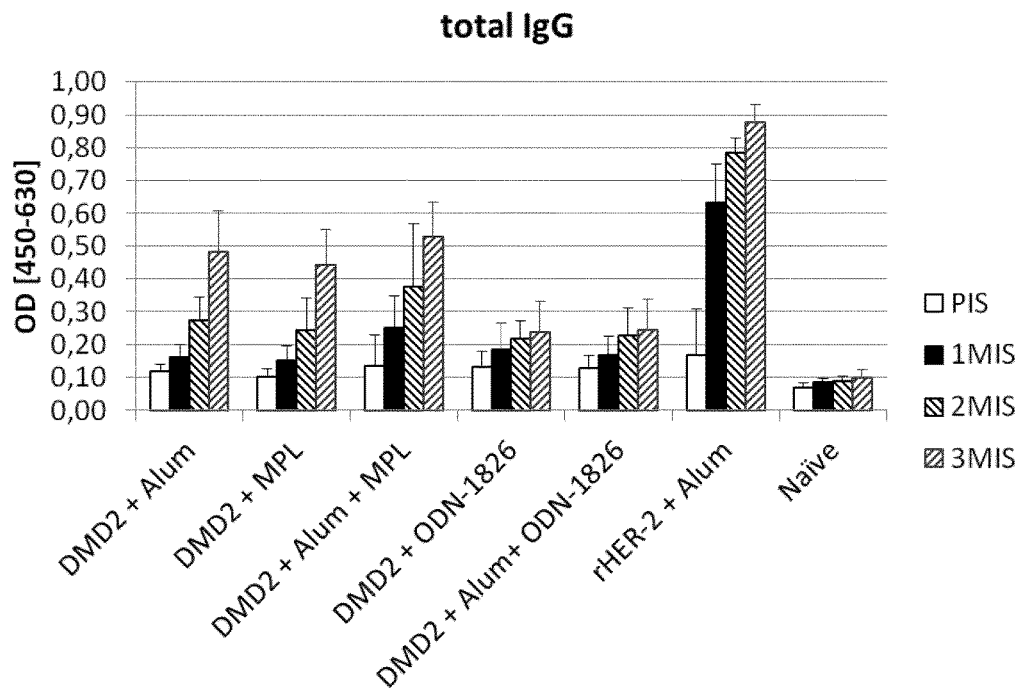

FIG. 8a) shows HER-2 specific total IgG levels induced by DMD2 in combination with different adjuvants (a) and HER-2 specific total IgG levels induced by DMD2 in combination with different adjuvants (b).

EXAMPLES

1. Screening of AAV Library for Trastuzumab Binders

A phenotye and genotype coupled AAV2 library comprising an $(NNK)_{15}$ insert (with N=A, G, C or T and K=G or T) and an upstream AAAGGG linker and a downstream GGGSG linker inserted after amino acid $N_{587}$ of the VP proteins was constructed with slight modifications as described in Perabo et al. (2003) and Büning et al. (2008, examples 1 and 2), leading to a diversity of about $3.6 \times 10^6$ viruses. Accordingly, the sequence of the library at $N_{587}$ was:

```
3949                    NotI
ctc cag gca ggc aac gcg gcc gca gga ggt gga
 L   Q  A585 G  N587 A   A   A   G   G   G BspEI
(NNK)15 ggt ggc ggt tcc gga gca caa gca gct
  x15    G   G   G   S   G  A588  Q   A   A acc gca (SEQ ID NO: 167)
 T   C  (SEQ ID NO: 168)
```

Screening for trastuzumab binding AAV2 insertion mutants was carried out similar to the methods described in Perabo et al. (2003) and Büning et al. (2008). In brief, commercially available monoclonal anti-HER2 antibody trastuzumab (Roche, Basel) was immobilized through its Fc-part to Protein G coupled Dynabeads (Immunprecipitation Kit, Invitrogen) and subsequently incubated with the AAV2 library from above. Alternatively, Protein A coupled MagnaBind beads (Thermo Scientific) were used as a matrix. Non-bound and unspecifically bound viruses were washed away under stringent conditions, whereas DNA from bound viruses was isolated. Such DNA was used as a template for a subsequent PCR amplification (Phusion High-Fidelity PCR Kit, Finnzymes) of the cap fragment comprising the insertion. The band of correct size was isolated (a representative agarose gel of a PCR amplification is shown in FIG. 1) and cloned back into the AAV2 encoding plasmid pUCAV2 (Hörer and Hallek 2005). Resulting clones were on the one hand sequenced; on the other hand they were used to generate a new library (library of the first selection round) by transfecting the DNA into 293-T cells and producing viruses as described in example 0. Each time 95 clones of the selection round were sequenced with respect to their respective inserted sequence at amino acid $N_{587}$ of the VP proteins. The generated library of first round had a diversity of about $10^6$. As expected, the first selection round did not yet lead to a marked enrichment of sequences.

Therefore, selection was repeated using the library of the first selection round, resulting in the library of the second selection round. After the second selection round, 9 clones had been enriched (at least two times present in the sequenced sample), the most frequent clone was found 8 times. Accordingly, diversity of the library was still sufficient to make a further selection round and the library of the second selection round was subjected to a third selection round. Again, 95 clones were sequenced with 23 sequences not being evaluated due to not being readable, having one or more inserts, containing mixed sequences (more than one sequence was sequenced) or incomplete sequences (linker missing or stop codon). From the 72 sequences that were evaluated more than half of the sequences had similarities with each other resulting in the definition of a first consensus sequence (see below).

A number of selections was carried out according to the above scheme with slight variations e.g. with different or alternating matrices (Dyna beads versus MagnaBind beads) or negative preselection against an antibody of the same isotype to avoid selection of binders to beads or antibody outside of the idiotype determining region of trastuzumab as generally suggested earlier (Büning et al. 2008).

The various screenings lead to the identification of inserted amino acid sequences as shown in Table 1.

TABLE 1

Frequency of identified amino acid insertions in third screening rounds

| Internal Ref. | AA Sequence | SEQ ID NO | Sum of 3. and 4. rounds |
|---|---|---|---|
| DMD01 | RLVPVGLERGTVDWV | SEQ ID NO: 1 | 108 |
| DMD02 | TRWQKGLALGSGDMA | SEQ ID NO: 2 | 24 |
| DMD03 | RTWQSGMADGEEIGR | SEQ ID NO: 3 | 25 |
| DMD04 | QVSHWVSGLAEGSFG | SEQ ID NO: 4 | 6 |
| DMD05 | SSWAAGTAAGDFKGY | SEQ ID NO: 5 | 37 |
| DMD06 | LSHTSGRVEGSVSLL | SEQ ID NO: 6 | 55 |
| DMD07 | SLWLLGRADGVSSGH | SEQ ID NO: 7 | 3 |
| DMD08 | QGRAKNLPNCGSGQR | SEQ ID NO: 8 | 1 |
| DMD09 | RSFEKFGGMKERLHC | SEQ ID NO: 9 | 1 |
| DMD10 | AVEPCITAHKSYMRV | SEQ ID NO: 10 | 1 |
| DMD11 | STLWHRGLAAGDVSR | SEQ ID NO: 11 | 1 |
| DMD12 | SESGVFVLQSCAWEY | SEQ ID NO: 12 | 1 |
| DMD13 | WGNCPLSSGGPKTFR | SEQ ID NO: 13 | 1 |

TABLE 1-continued

Frequency of identified amino acid insertions in third screening rounds

| Internal Ref. | AA Sequence | SEQ ID NO | Sum of 3. and 4. rounds |
|---|---|---|---|
| DMD14 | WVGSRSMWAECGLDE | SEQ ID NO: 14 | 1 |
| DMD15 | LDSTSLAGGPYEAIE | SEQ ID NO: 15 | 4 |
| DMD16 | LSRCGKPMDVEAALN | SEQ ID NO: 16 | 1 |
| DMD17 | FPKSQVSRGEMRLGG | SEQ ID NO: 17 | 1 |
| DMD18 | FFSGRWSEGTALGSS | SEQ ID NO: 18 | 1 |
| DDD19 | HVVMNWMREEFVEEF | SEQ ID NO: 19 | 6 |
| DDD20 | GVAWSSGQAHGSRTE | SEQ ID NO: 20 | 7 |
| DDD21 | WDSGDAVGNEVLLVG | SEQ ID NO: 21 | 5 |
| DDD22 | WKMGTAQGSGQDGEY | SEQ ID NO: 22 | 27 |
| DDD23 | GWNSGKVDGGAGRSM | SEQ ID NO: 23 | 5 |
| DDD24 | LVGVWPVMVETVYET | SEQ ID NO: 24 | 2 |
| DDD25 | QWLEGLAEGMVHTLG | SEQ ID NO: 25 | 5 |
| DDD26 | DPYESSRSTLLRAAR | SEQ ID NO: 26 | 3 |
| DDD27 | GDEEMWPIVRELQSL | SEQ ID NO: 27 | 2 |
| DDD28 | LKWYSGELEGSKELL | SEQ ID NO: 28 | 1 |
| DDD29 | NPGTWERGVAAGDIE | SEQ ID NO: 29 | 1 |
| DDD30 | QTKWPIATEVWRETV | SEQ ID NO: 30 | 4 |
| DDD31/DDM51 | VGAAAQWPEVREYLM | SEQ ID NO: 31 | 3 |
| DDD32 | YFSGKAEGREAPSWD | SEQ ID NO: 32 | 1 |
| DMM33 | CDVQLASAKKRYLGV | SEQ ID NO: 33 | 1 |
| DMM34 | CMGVVKAWDSIRLVE | SEQ ID NO: 34 | 1 |
| DMM35 | DVGQGRRKSLNLECF | SEQ ID NO: 35 | 1 |
| DMM36 | DVTWRHKHIVTKGGL | SEQ ID NO: 36 | 1 |
| DMM37 | GGYEVRKHFQSREVV | SEQ ID NO: 37 | 1 |
| DMM38 | KNCDRLSWSGARNLS | SEQ ID NO: 38 | 1 |
| DMM39 | LVEHWSRSKKSSFEF | SEQ ID NO: 39 | 1 |
| DMM40 | LVSVQKKWERKAESM | SEQ ID NO: 40 | 1 |
| DMM41 | MFLSDKYSREPHKGK | SEQ ID NO: 41 | 1 |
| DMM42 | RRTLCGTGSEMVLFK | SEQ ID NO: 42 | 1 |
| DMM43 | SVRLSSAQGCINMVV | SEQ ID NO: 43 | 1 |
| DMM44 | SWASGMAVGSVSFEE | SEQ ID NO: 44 | 1 |
| DMM45 | VTGNCKGSRQQHVLG | SEQ ID NO: 45 | 1 |
| DMM46 | WWAHGEDITGHSLCL | SEQ ID NO: 46 | 1 |
| DDM47 | ASQGSWKLGTARGSG | SEQ ID NO: 47 | 3 |
| DDM48 | MQLICRTSLREERII | SEQ ID NO: 48 | 2 |
| DDM49 | RFSCAVGKECSHKQC | SEQ ID NO: 49 | 1 |
| DDM50 | RSNDVLGCKLRVVGC | SEQ ID NO: 50 | 1 |
| DDM52 | WAFGLALGSLETIDL | SEQ ID NO: 52 | 1 |
| DDM53 | WGEPYSGKGSHGKIG | SEQ ID NO: 53 | 1 |
| DDD54 | ASAWLLGNVEGSEIR | SEQ ID NO: 54 | 2 |
| DDD55 | CQWRAGTAVGSSVGN | SEQ ID NO: 55 | 1 |
| DDD56 | HEVLWGEMDAPWVVP | SEQ ID NO: 56 | 2 |
| DDD57 | IASGWSVGWADGDDS | SEQ ID NO: 57 | 1 |
| DDD58 | PYEELVATRSRAGGM | SEQ ID NO: 58 | 2 |
| DDD59 | SCLARVHCDMPREWE | SEQ ID NO: 59 | 1 |
| DDD60 | VATKGVTLWETGLAE | SEQ ID NO: 60 | 1 |
| DDD61 | VTLMKISKWDAGLAE | SEQ ID NO: 61 | 1 |
| DDD62 | WMSGQSDGSSGGGPK | SEQ ID NO: 62 | 4 |
| DDDD63 | REAGQWARGLAVGSC | SEQ ID NO: 63 | 1 |
| DDDD64 | YVIGPYERECELGMG | SEQ ID NO: 64 | 1 |
| DDDD65 | WKMGMAQGSGQDGEY | SEQ ID NO: 65 | 1 |

2. Alignment Analysis of Identified Sequences

Sequence alignments using the MultAlin algorithm (Corpet 1988) of all identified sequences and subgroups of identified sequences lead to the identification of consensus sequences. The most frequently found motif is the amino acid sequence WxxGxAxGS (consensus 1, SEQ ID NO: 51), which was found in 21 individual sequences (Table 2). More specifically, this consensus sequence can be defined as (SEQ ID NO: 66)
(W/H/Y/V)xxGx(A/L/V/C/E)xG(S/M/D/E/V/N/G/R/T), (SEQ ID NO: 67)
WxxGx(A/V/L)xG(S/T/M/D/E), (SEQ ID NO: 68)
Wx(S/T/K/R/M/L/A/V)Gx(A/V)xG(S/M/D), (SEQ ID NO: 69)
Wx(K/R/E/S/T/F)G(L/M/T/V)A(A/V/L/E/D)G(S/T/D/E/M), (SEQ ID NO: 70)
(S/T/G)(S/T/R/Q/H/L)Wx(K/R/S/E/F)G(L/M/T/V)A(A/V/L/E)G(S/D/M)(G/V/L/I/S/C/F), (SEQ ID NO: 71)
(S/T/L/Q)Wx(M/A/L/V)G(T/A/S/M)A(Q/A/V/H/K/R)G(S/T/D/E), (SEQ ID NO: 72)
(S/T/G)(S/T/Q)W(K/R/A)(M/A/L)G(T/A/M)A(Q/A/V/R)G(S/D)(G/F/S)(Q/K/V)(D/G), (SEQ ID NO: 73)
Wx(S/T/A/L/V)Gx(A/V)(E/D/A/V/H/K/R)G(S/T/D/E/N/G/V), -continued (SEQ ID NO: 74)
(S/R/V)xWx(S/L/V)G(Q/R/N/M/W/D)(A/V/S)(E/D/V/H)
G(S/D/E/N/V)(E/D/S/R).

TABLE 2

Alignment of amino acid insertion of consensus 1

| Internal Ref. | AA Sequence | SEQ ID NO |
|---|---|---|
| DMD02 | TRWQKGLALGSGDMA | SEQ ID NO: 2 |
| DMD18 | FFSGRWSEGTALGSS | SEQ ID NO: 18 |
| DDDD63 | REAGQWARGLAVGSC | SEQ ID NO: 63 |
| DDD29 | NPGTWERGVAAGDIE | SEQ ID NO: 29 |
| DMD11 | STLWHRGLAAGDVSR | SEQ ID NO: 11 |
| DMM44 | SWASGMAVGSVSFEE | SEQ ID NO: 44 |
| DDM52 | WAFGLALGSLETIDL | SEQ ID NO: 52 |
| DDD25 | QWLEGLAEGMVHTLG | SEQ ID NO: 25 |
| DMD04 | QVSHWVSGLAEGSFG | SEQ ID NO: 04 |
| DDD22 | WKMGTAQGSGQDGEY | SEQ ID NO: 22 |
| DDDD65 | WKMGMAQGSGQDGEY | SEQ ID NO: 65 |
| DDM47 | ASQGSWKLGTARGSG | SEQ ID NO: 47 |
| DMD05 | SSWAAGTAAGDFKGY | SEQ ID NO: 05 |
| DDD55 | CQWRAGTAVGSSVGN | SEQ ID NO: 55 |
| DMD03 | RTWQSGMADGEEIGR | SEQ ID NO: 03 |
| DMD07 | SLWLLGRADGVSSGH | SEQ ID NO: 07 |
| DDD62 | WMSGQSDGSSGGGPK | SEQ ID NO: 62 |
| DDD20 | GVAWSSGQAHGSRTE | SEQ ID NO: 20 |
| DDD54 | ASAWLLGNVEGSEIR | SEQ ID NO: 54 |
| DDD57 | IASGWSVGWADGDDS | SEQ ID NO: 57 |
| DDD21 | WDSGDAVGNEVLLVG | SEQ ID NO: 21 |
| Consensus 1 | WxxGxAxGS | SEQ ID NO: 51 |

Another six sequences were identified with the same motif but lacking the N-terminal W (Table 3), therefore being defined as the incomplete consensus 1 GxAxGS (SEQ ID NO: 75). More specifically, this consensus sequence can be defined as (SEQ ID NO: 76)
(W/H/Y/V)x(S/T/A/V/L)Gx(A/V/L/C/E)(E/D/K/R/H)
G(S/T/G/V/R),
or (SEQ ID NO: 77)
(L/R)x(W/H/Y/V)x(S/T/V)G(K/R/N/E/L)(A/V/L/C/E)
(E/D/K/R)G(S/T/G/R)xx(L/R/P/Q/W).

TABLE 3

Alignment of amino acid insertion of incomplete consensus 1

| Internal Ref. | AA Sequence | SEQ ID NO |
|---|---|---|
| DDD28 | LKWYSGELEGSKELL | SEQ ID NO: 28 |
| DMD06 | LSHTSGRVEGSVSLL | SEQ ID NO: 06 |
| DDD23 | GWNSGKVDGGAGRSM | SEQ ID NO: 23 |
| DDD32 | YFSGKAEGREAPSWD | SEQ ID NO: 32 |
| DMM45 | VTGNCKGSRQQHVLG | SEQ ID NO: 45 |
| DMD01 | RLVPVGLERGTVDWV | SEQ ID NO: 01 |
| Inc. Consensus 1 | GxAxGS | SEQ ID NO: 75 |

Seven sequences were grouped to consensus 2 being WxxxxxSRGxxR (SEQ ID NO: 78) as shown in Table 4. More specifically, this consensus sequence can be defined as (SEQ ID NO: 79)
(W/F/K)x(N/K/H/E/S/C)xxx(S/G/I/V)(S/T/K/R/W)
(G/S/E/K), (SEQ ID NO: 80)
(W/F)x(N/H/K/E)xxx(S/G/I/V)(S/T/K/R)(G/K)
(G/E/S/H)x(R/K/L/G),,
or (SEQ ID NO: 81)
(F/K)xx(S/D)xxS(R/W)(G/S/E)(G/E/P)x(R/K).

TABLE 4

Alignment of amino acid insertion of consensus 2

| Internal Ref. | AA Sequence | SEQ ID NO |
|---|---|---|
| DDM53 | WGEPYSGKGSHGKIG | SEQ ID NO: 53 |
| DMD13 | WGNCPLSSGGPKTFR | SEQ ID NO: 13 |
| DMM46 | WWAHGEDITGHSLCL | SEQ ID NO: 46 |
| DMD17 | FPKSQVSRGEMRLGG | SEQ ID NO: 17 |
| DMM38 | KNCDRLSWSGARNLS | SEQ ID NO: 38 |
| DMM41 | MFLSDKYSREPHKGK | SEQ ID NO: 41 |
| DMM36 | DVTWRHKHIVTKGGL | SEQ ID NO: 36 |
| Consensus 2 | WxxxxxSRGxxR | SEQ ID NO: 78 |

Seven sequences were grouped to consensus 3 being RSxSxxGGPxE (SEQ ID NO: 82) as shown in Table 5. More specifically, this consensus sequence can be defined as (SEQ ID NO: 83)
(R/D)(S/T/F/L)x(E/D/S/C)xxG(G/C/S/K), (SEQ ID NO: 84)
RSx(E/D)xxG(G/C)xx(E/D/R)(V/A/L/R),
or (SEQ ID NO: 85)
(R/D)(S/T/F/L)(S/T/L)(S/C)xxG(G/C/S/K)(P/E/I)
(M/N/C/Y)(E/D/V/S/M)(V/A/L/H).

TABLE 5

Alignment of amino acid insertion of consensus 3

| Internal Ref. | AA Sequence | SEQ ID NO |
|---|---|---|
| DMD09 | RSFEKFGGMKERLHC | SEQ ID NO: 9 |
| DDM50 | RSNDVLGCKLRVVGC | SEQ ID NO: 50 |
| DMD15 | LDSTSLAGGPYEAIE | SEQ ID NO: 15 |
| DMM43 | SVRLSSAQGCINMVV | SEQ ID NO: 43 |
| DMM42 | RRTLCGTGSEMVLFK | SEQ ID NO: 42 |
| DDM49 | RFSCAVGKECSHKQC | SEQ ID NO: 49 |
| DMD16 | LSRCGKPMDVEAALN | SEQ ID NO: 16 |
| Consensus 3 | RSxSxxGGPxE | SEQ ID NO: 82 |

Eight sequences were grouped to consensus 4 being VxxxxxREE (SEQ ID NO: 86) as shown in Table 6. More specifically, this consensus sequence can be defined as (SEQ ID NO: 87)
(K/R/M/G/D)x(W/Y/S/T/F/I)x(R/N/S/T/L)(K/R/E/D/L), (SEQ ID NO: 88)
(D/G)x(Y/Q/T/G)(E/W/Q/L)x(H/R/S/C)(K/R)(K/H/S/T)
(S/T/F/I)(L/V/Q)(R/N/S/T/L)(K/R/E/L)(E/A/G),
or (SEQ ID NO: 89)
(V/L/I)(S/V/I)(K/R/M/G/D)(K/H/N/P)(W/Y)x(R/N)
(E/D)(E/C/P)

TABLE 6

Alignment of amino acid insertion of consensus 4

| Internal Ref. | AA Sequence | SEQ ID NO |
|---|---|---|
| DMM36 | DVTWRHKHIVTKGGL | SEQ ID NO: 36 |
| DMM37 | GGYEVRKHFQSREVV | SEQ ID NO: 37 |
| DDD26 | DPYESSRSTLLRAAR | SEQ ID NO: 26 |
| DMM35 | DVGQGRRKSLNLECF | SEQ ID NO: 35 |
| DDM48 | MQLICRTSLREERII | SEQ ID NO: 48 |
| DDD19 | HVVMNWMREEFVEEF | SEQ ID NO: 19 |
| DDDD64 | YVIGPYERECELGMG | SEQ ID NO: 64 |
| DMM41 | MFLSDKYSREPHKGK | SEQ ID NO: 41 |
| Consensus 4 | VxxxxxREE | SEQ ID NO: 86 |

Twelve sequences were grouped to consensus 5 being VGxxxxWPxVRE (SEQ ID NO: 90) as shown in Table 7. More specifically, this consensus sequence can be defined as (SEQ ID NO: 91)
(G/A/S)x(A/V/I/R/E/Q)(K/S/T/A/G/E)x(W/L)
(P/D/E/A/G/S)xxx(E/S/L/K/A), (SEQ ID NO: 92)
(G/A)x(A/V/R)(K/S)x(W/L)(P/A)(N/E)CG(S/L)x(E/Q), (SEQ ID NO: 93)
(G/S)x(A/V/E/Q)(A/K/E)xW(P/D/E)(I/E/R/S/T)
(I/V/K)(R/A/G)(E/L)x(E/Q/L/M), (SEQ ID NO: 94)
(V/Q/E)(E/G/T/V)(K/L/V/H)W(P/S/D/E/G)
(I/A/V/E/R/S/T)x(K/V/T/D)(E/K/A)(V/S/T/P/E)
(S/V/W),
or (SEQ ID NO: 95)
(V/I)(S/T)(L/K)W(D/E)xGLAE.

TABLE 7

Alignment of amino acid insertion of consensus 5

| Internal Ref. | AA Sequence | SEQ ID NO |
|---|---|---|
| DMD8 | QGRAKNLPNCGSGQR | SEQ ID NO: 8 |
| DMD14 | WVGSRSMWAECGLDE | SEQ ID NO: 14 |
| DMM34 | CMGVVKAWDSIRLVE | SEQ ID NO: 34 |
| DDD27 | GDEEMWPIVRELQSL | SEQ ID NO: 27 |
| DDD31/DDM51 | VGAAAQWPEVREYLM | SEQ ID NO: 31 |
| DMM40 | LVSVQKKWERKAESM | SEQ ID NO: 40 |
| DMM39 | LVEHWSRSKKSSFEF | SEQ ID NO: 39 |
| DDD24 | LVGVWPVMVETVYET | SEQ ID NO: 24 |
| DDD30 | QTKWPIATEVWRETV | SEQ ID NO: 30 |
| DDD56 | HEVLWGEMDAPWVVP | SEQ ID NO: 56 |
| DDD60 | VATKGVTLWETGLAE | SEQ ID NO: 60 |
| DDD61 | VTLMKISKWDAGLAE | SEQ ID NO: 61 |
| Consensus 5 | VGxxxxWPxVRE | SEQ ID NO: 90 |

Four sequences were grouped to consensus 6 being VxLxSAxKxYxxV (SEQ ID NO: 96) as shown in Table 8. More specifically, this consensus sequence can be defined as (SEQ ID NO: 97)
(E/D/V/A)(P/Q/N/E/RL/C)(I/A/V/S/T)(S/T/A)(A/T)
(H/K/R/Q)(S/K/G)(R/S/C)(Y/A/I/V)xx(V/A/M), (SEQ ID NO: 98)
(E/V)(P/Q)(L/C)(I/A/V)(S/T/A)A(H/K/R)K(R/S)YxxV,
or (SEQ ID NO: 99)
(E/V)(E/R/Q)(L/C)(V/S)(S/T/A)(A/T)(R/Q)(S/K/G)
(R/S/C)(A/I/V)xx(V/M)

Table 8: Alignment of amino acid insertion of consensus 6

| Internal Ref. | AA Sequence | SEQ ID NO |
|---|---|---|
| DMD10 | AVEPCITAHKSYMRV | SEQ ID NO: 10 |
| DMM33 | CDVQLASAKKRYLGV | SEQ ID NO: 33 |
| DDD58 | PYEELVATRSRAGGM | SEQ ID NO: 58 |

-continued

| Internal Ref. | AA Sequence | SEQ ID NO |
|---|---|---|
| DMM43 | SVRLSSAQGCINMVV | SEQ ID NO: 43 |
| Consensus 6 | VxLxSAxKxYxxV | SEQ ID NO: 96 |

Identified sequences of DMD12 and DDD59 were not grouped into one of these consensus sequences.

3. Production of AAV and AAV Like Particles 3.1. Manufacturing of AAV (Virus) in Mammalian Cells Manufacturing of AAV (virus) in mammalian cells was performed as described by Sonntag et al. (2010a, examples 1.2 to 1.4). Briefly, AAV manufacturing was carried out by co-transfection of 293-T cells with an AAV encoding plasmid (pUCAV2) with a cap gene containing the respective mimotope DNA sequence insertion and the helper plasmid pUCAdV to provide adenoviral helper functions. The construction of pUCAV2 as an AAV encoding plasmids is described in detail in Hörer and Hallek (2005). Plasmid pTAV2.0 is described in Heilbronn (1990), pVP3 is described in Warrington (2004).

3.2. Manufacturing of AAVLP (Virus-Like Particles) in Mammalian Cells

Transfection of cells was carried out as described by Sonntag et al. (2010a). Briefly, 293-T cells (ATCC, Manassas, USA) were seeded and after 24 h transfected with 36 µg per 145 cm² dish pCI-VP2mutACG containing the respective insertion by calcium phosphate precipitation. 293-T cells were harvested 70 to 72 h after transfection with a cell lifter, transferred into plastic tubes (Falcon) and centrifuged. The cell pellet was resuspended in lysis buffer (150 mM NaCl, 50 mM Tris, pH 8.5) and objected to freeze and thaw cycles (liquid nitrogen/37° C.). The cell lysate was cleared by centrifugation and the AAV-containing supernatant was used for further purification. Alternatively the whole dishes were objected to three freeze and thaw cycles (−50° C./RT). The remaining supernatant of centrifugation or, alternatively, flow through of filtration was collected and further purified as described in below.

3.3. Purification of AAV by Density Gradient Centrifugation Using Iodixanol

AAV particles were purified by iodixanol gradient centrifugation according to example 4.3 of (Büning et al. 2008).

3.4. Purification of AAV Like Particles by Chromatography

Purification of AAV like particles containing HER2 mimotopes was carried out as described by Sonntag et al. (2010a, examples 1.3). Briefly, the freeze-thawed, cleared lysate containing modified AAVLPs was diluted by adding Hepes buffer (pH 6.0) without NaCl until a conductivity of approximately 3 to 9 mS/cm was reached, the pH of the lysate had been adjusted to 5.5-7.5 depending on the modified AAVLPs and the preparation was cleared by a filtration cascade with two filter capsules (Sartopure PP2, 5 µm and Sartopore PP2, 0.65 µm, Sartorius-Stedim, Göttingen, Germany). The filtrate was bound to a Cation exchange chromatography (Fractogel EMD $SO_3^-$ (M) chromatography column, XK16, Merck, Darmstadt, Germany), washed and bound particles were eluted with sodium chloride. A buffer exchange was performed (Sephadex G25 packed chromatography column, XK26, GE Healthcare, Munich, Germany) in order to continue with an anion exchange chromatography (CaptoQ chromatography column; XK16, GE Healthcare, Munich, Germany). After equilibration, the protein fraction obtained after buffer exchange was loaded and the flow-through containing 90% of the particles was collected. The flow-through containing AAVLPs was concentrated using Vivacell 100 units (MWCO 100,000, Sartorius-Stedim) and a swinging-bucket rotor (MULIFUGE L-R; Heraeus, Hanau, Germany). Resulting concentrate was immediately separated through a size exclusion chromatography (Superdex 200, prep grade, XK50, GE Healthcare, Munich, Germany) which was packed and equilibrated using running buffer consisting of 200 mM NaCl, 50 mM HEPES (pH 6.0), 2.5 mM $MgCl_2$. Particles were loaded onto the column and eluted first in the first SEC fractions. SEC fractions with a particle purity of greater than 95% were pooled, sterile filtered and stored at −80° C.

Exemplary titers yielded by small scale production and purification are shown in Table 9. Interestingly, titers of AAV clones containing a trastuzumab mimotope identified by the screening methods as described herein typically yielded higher titers as compared to wild type AAV2. This was not expected as the identified AAV clones each contain a 26 AA insert that potentially may interfere with the expression and/or assembly of the AAV capsid proteins. The absence of AAV clones showing lower titers (compared to wild type AAV2) documents that the described screening methods not only select for AAVs that bind to trastuzumab but also for AAVs that have an equal or more efficient expression and/or assembly of the capsid proteins. This of course is a welcome effect as high yields are of course very important for vaccine candidates.

TABLE 9

Titers of AAV clone productions and purifications.

| | Concentration [particle/ml] |
|---|---|
| DMD01 | $1.12 \times 10^{13}$ |
| DMD02 | $4.13 \times 10^{13}$ |
| DMD03 | $1.51 \times 10^{13}$ |
| DMD04 | $2.29 \times 10^{13}$ |
| DMD05 | $3.63 \times 10^{13}$ |
| DMD06 | $3.80 \times 10^{13}$ |
| DMD07 | $1.63 \times 10^{13}$ |
| DMD15 | $1.91 \times 10^{13}$ |
| DMD18 | $1.60 \times 10^{13}$ |
| DDD19 | $6.30 \times 10^{13}$ |
| DDD21 | $1.98 \times 10^{13}$ |
| DDD30 | $1.50 \times 10^{13}$ |
| DDD31 | $1.92 \times 10^{13}$ |
| wtAAV2 | $9.07 \times 10^{12}$ |

4. Sandwich ELISA with AAVs from Cell Lysate

In order to quickly determine whether identified AAVs containing putative HER2 mimotopes specifically interact with the trastuzumab (Roche) AAVs directly within cell lysate were tested in a sandwich ELISA by testing whether trastuzumab can be bound to clones immobilized on the ELISA plate. ELISA plates having A20 mAb on the surface of the plates (AAV2 titration ELISA kit, Progen) were used in order to immobilize identified AAV clones from cell lysates (after freeze thaw lysis, 100 μl of 1:10 dilution in sample buffer from ELISA kit) as previously described (Grimm et al. 1999). As a negative control a different humanized IgG-1 monoclonal antibody was used instead of trastuzumab. Additionally, wild type AAV like particles were used in order to detect unspecific binding of trastuzumab to AAV.

Bound AAVs were incubated with trastuzumab (100 μl of a 10.0 μg/ml solution in PBS/0.01 Tween-20) or with the humanized IgG-1 mAb (identical concentration) and detected with HRP-labeled human anti IgG antibodies (Bethyl #A80-319P, 100 µl of a 1:2,500 dilution in PBS/ 0.1% Tween-20) by OD measurement at 450 nm ($OD_{450}$) in an ELISA reader (ER02). Values of blank (empty wells only with buffer) were subtracted from determined values of the individual clones.

Figure 2:
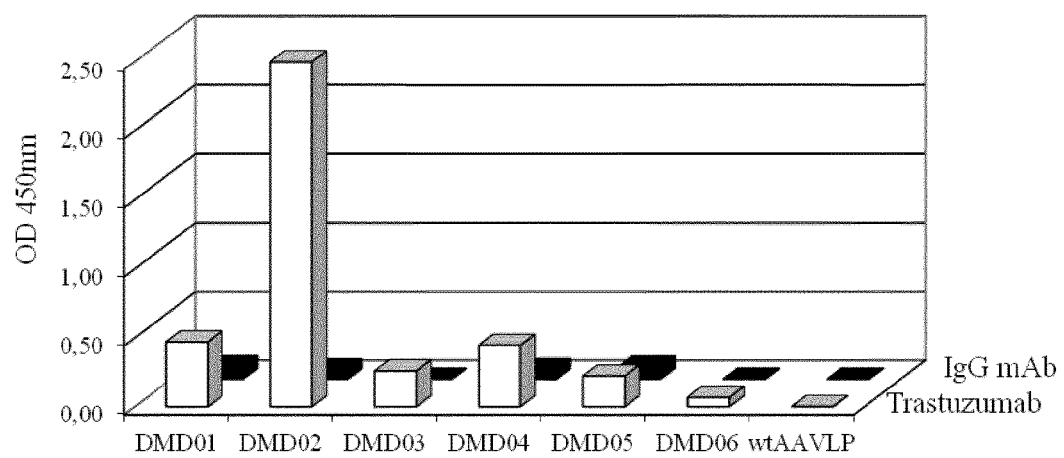
Figure 3:
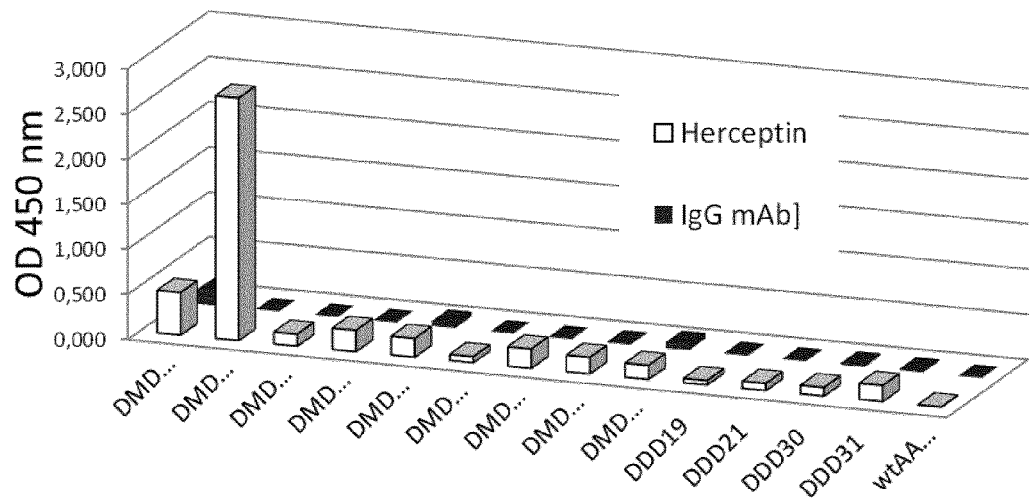
Figure 4:
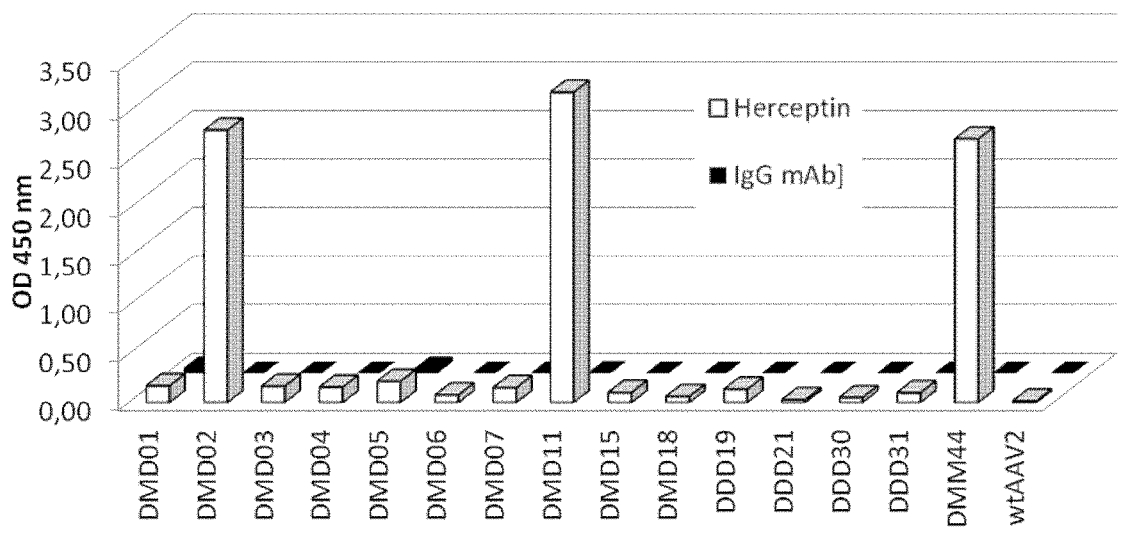

FIG. 2 shows an example of the Sandwich ELISA from cell lysates for the AAV clones DMD1 to DMD6. This ELISA was repeated for all identified AAV clones. Results were grouped according to the following scheme:

| | | |
|---|---|---|
| +++ | stands for $OD_{450}$ | >1.0, |
| ++ | for $OD_{450}$ | >0.5, |
| + | for $OD_{450}$ | >0.2, |
| +/− | for $OD_{450}$ | >0.1, and |
| − | for $OD_{450}$ | <0.1. | and results for all clones are summarized in Table 11, columns two and three.

A number of clones selected from the AAV library showed high specificity for trastuzumab compared to the humanized IgG-1 monoclonal antibody control (e.g. DMD02, DMD11, DMM44, DDD21, DMM33), whereas only few clones were rather unspecific within this sandwich ELISA from cell extracts—having a higher reactivity with the IgG mAb control compared to the trastuzumab (DMM45, DMM38, DMM37) or a very reactivity to both antibodies (DMM33).

Therefore it is concluded that the selections generally yielded a meaningful set of AAVs containing at the surface more or less specific mimotopes for soluble trastuzumab. For interpreting data from the sandwich ELISA it has to be understood that, while the tested AAV clones each have 60 copies of the inserted mimotope on the surface, the monoclonal antibody in the ELISA test has only two binding sites for the mimotope. During the selection however, when the selection antibody trastuzumab was immobilized on beads, multiple antibody binding sites can cooperate in retracting matching AAV clones. For the use of identified clones in immunization, the situation for binding the AAV may be more comparable to the selection conditions, as a B-cell response is triggered by binding B-cells to the antigen through membrane bound IgM, where also multiple IgM molecules on the surface of the B-cell can cooperatively bind to multiple epitopes on virus—which exactly is the reason why virus/virus-like particles are potent immunogens. Therefore, it can be assumed that the affinity of a screened AAV clone to the soluble antibody is not the only determining feature for activity in immunization experiments.

5. ELISA with Purified AAVs

In order to validate affinities observed for AAV clones from cell lysates (example 4) purified AAV particles (see example 0) were analyzed again in two different ELISA systems for their affinity to trastuzumab similar to example 4. Clones were tested in two different settings.

In the indirect ELISA AAV particles (100 μl of a $1\times10^{11}$ particle/ml dilution) were directly bound to the ELISA plate, unbound binding sites saturated (5% milk powder in PBS/0.1% Tween-20) and trastuzumab (100 μl of a 10 μg/ml dilution in PBS/0.01% Tween-20) or a different humanized IgG-1 monoclonal antibody as a negative control added. Bound antibodies were detected and evaluated as described above. Results of an exemplary ELISA are depicted in FIG. 3.

In the sandwich ELISA A20 monoclonal antibodies coated ELISA plates (Progen #PRATV) were used to immobilize the AAV particles (100 μl of a $1\times10^{11}$ particle/ml dilution in sample buffer of the Progen ELISA kit) and subsequently trastuzumab (100 μl of a 10 μg/ml dilution in PBS/0.01% Tween-20) or a different humanized IgG-1 monoclonal antibody as a negative control added. Again, bound antibodies were detected with HRP-coupled anti-human IgG. Wild type AAV particles are used as negative control for unspecific binding of the antibodies to the AAV particles. Bound antibodies were detected and evaluated as described above. Results of an exemplary ELISA are depicted in FIG. 4.

6. Sandwich ELISA in Presence of Chaotopic Agent

In order to determine the stability of the interaction between AAV clones and trastuzumab a modified sandwich ELISA of example 4 was done in the presence of a chaotropic agent, i.e. urea, as a measure for avidity (strength of a multivalent interaction between antibody and antigen). Determination of the avidity of the AAV/antibody interaction is based on the disruption of weak interactions by chaotropic substances like urea.

First, AAV clones ($10^{10}$ particle in 100 μl; exception DMD11 where only half of the amount was coated due to low availability of material) were coated over night/4° C. onto an ELISA plate, washed, remaining/unspecific binding blocked with 5% milk powder solution in PBS/0.1% Tween-20 and two different amounts of trastuzumab (as indicated in Table 10 in 100 μl) added.

In a pre-experiment the optimal concentration of trastuzumab had been determined Optimal conditions for measuring the avidity are if $OD_{450}$ values are equal or larger than 0.4 in order to discriminate against background. Therefore, for AAV clones individual trastuzumab concentrations were determined and are shown in Table 10.

TABLE 10

Trastuzumab concentrations for avidity determination

| clones | trastuzumab concentrations [μg] |
|---|---|
| DMD01 | 5.0 and 10.0 |
| DMD02 | 5.5 and 1.0 |
| DMD03 | 5.0 and 10.0 |
| DMD04 | 2.0 and 5.0 |
| DMD05 | 2.0 and 5.0 |
| DMD06 | 5.0 and 10.0 |
| DMD07 | 5.0 and 10.0 |
| DMD11 | 0.1 and 0.2 |
| DMD18 | 5.0 and 10.0 |
| DDD19 | 5.0 and 10.0 |
| DDD30 | 5.0 and 10.0 |
| DMM44 | 0.5 and 10 |

After incubation with trastuzumab plates were again washed, first with PBS/0.1% Tween-20 and optionally three times for 5 min with 5 M urea in PBS/0.1% Tween-20, which is the wash step under denaturing/chaotropic conditions, followed by washing with PBS/0.1% Tween-20. Detection and $OD_{450}$ measurement was carried out as described in example 4.

The avidity index was calculated according to the formula $$\frac{OD450\text{ with chaotropic wash} - OD450\text{ blank}}{OD450\text{ without chaotropic wash} - OD450\text{ blank}} \cdot 100 = \%\text{ avidity}$$

Averages with standard deviations for resulting avidity indices are depicted as an example for clones AAVs DMD01 to DMD07, DMD11, DMD18, DDD19, DDD30 and DMM44 in FIG. 5. This ELISA under chaotropic conditions was repeated for a number of further AAV clones. Results were grouped according to the following scheme:

| | | | |
|---|---|---|---|
| +++ | | avidity index | >30% |
| ++ | 15% ≤ | avidity index | ≤30% |
| + | | avidity index | <15% | and are summarized in Table 11, column four.

Interestingly, avidity indices of the AAV clones do not correlate with the affinities determined both with crude cell lysates and purified AAV particles. For example, DMD02, DMD11 and DMM44 have shown high affinities for trastuzumab, whereas the avidity indices of these clones are rather low. On the other side, DMD04, DMD06 and DDD19 have a low affinity to trastuzumab, whereas their avidity indices are rather high. It should be noted that for DDD19 the correlation between $OD_{450}$ and avidity index could not be shown.

7. Immunization of Mice

BALBc mice were immunized with AAV clones and blood samples were taken after 2 or more immunizations. HER2 specific antibodies in the mice sera were determined by ELISA. Briefly, ELISA plates were coated with recombinant HER2 overnight at 4° C., washed and unspecific binding was blocked with 1% milk powder in PBS/0.05% Tween-20. Subsequently plates were incubated with 1:100 diluted sera or trastuzumab [1 μg/ml] overnight at 4° C. After washing the plates, bound antibodies were detected using a rat anti-mouse IgG followed by a goat anti-rat IgG coupled to HRP by OD measurement at 490 nm. PIS resembles pre-immune sera, MIS mouse sera after the respective immunization/boost. Results for pooled sera of 8 mice per indicated AAV clone are shown in FIG. 6. VP3-TTSN is an AAV control having an unspecific mimotope insert.

8. Proliferation Assay

Sera of BALBc mice immunized with AAV displaying mimotopes DMD01, DMD02, DMD04 and DMD06 as well as from naïve mice were purified with protein G sepharose (Incubation of mice sera overnight with Protein G-Sepharose beads; elution with 0.1 m Glycine-buffer; afterwards dialysis against PBS to reduce Glycine which acted in this concentration toxic on cell viability assays. Quality control in SDS-PAGE).

To test whether these purified antibodies act tumoricidic/tumoristatic on HER2 overexpressing cells, a cell viability assay with mBT474 human breast cancer cells was established. "m" means these cells were passaged once through SCID mice. This is important to enable better grafting for the planned consecutive SCID graft experiments. The assay using mBT474 cells was established with monoclonal trastuzumab IgG and rendered a 30% growth inhibition after 24 h. mBT474 cells were incubated with trastuzumab as positive control and an isotype control (1 μg/well), and compared to untreated cells alone (FIG. 7A). In the same assay mBT474 cells were incubated with purified IgG from pooled mouse sera from mice immunized with different AAV particles (DMD1, DMD2, DMD4, DMD6, FIG. 7B).). Readout was performed with the EZ4U cell proliferation assay (Biomedica, Vienna).

The different clones elicited various degrees of proliferation inhibition (all at 5 μg/well) compared to untreated cells alone. The effects on mBT474 seem to be most pronounced for DMD1-antibodies and they reach the effects of trastuzumab.

TABLE 11

Summary of functional characterization of HER2 AAV clones

| Clone | Trastuzumab Reactivity Cell lysate | IgG mAb Reactivity | Trastuzumab Reactivity Purified AAV | Avidity Index (5M urea) | rec. HER2 Reactivity (mice sera) | cellular HER2 Reactivity (mice sera) |
|---|---|---|---|---|---|---|
| Consensus 1 | | | | | | |
| DMD02 | +++ | − | +++ | + | +++/+ | + |
| DMD18 | + | − | +/− | + | | |
| DDDD63 | + | +/− | | | | |
| DDD29 | +/− | − | | | | |
| DMD11 | +++ | − | +++ | + | | |
| DMM44 | +++ | +/− | +++ | + | n.d./++ | |
| DDM52 | + | +/− | | | | |
| DDD25 | +/− | − | | | | |
| DMD04 | + | − | + | +++ | +/+++ | + |
| DDD22 | + | − | | | | |
| DDDD65 | +/− | − | | | | |
| DDM47 | + | + | | | | |
| DMD05 | + | − | ++ | ++ | | |
| DDD55 | + | − | | | | |
| DMD03 | + | − | + | ++ | | |
| DMD07 | + | − | + | ++ | + | + |
| DDD62 | +/− | − | | | | |
| DDD20 | +/− | +/− | + | | | |
| DDD54 | − | − | | | | |
| DDD57 | +/− | − | | | | |
| DDD21 | +++ | − | +/− | | +++ | + |
| Partial Consensus 1 | | | | | | |
| DDD28 | +/− | − | | | | |
| DMD06 | − | − | +/− | ++ | n.d./+++ | |
| DDD23 | + | + | | | | |
| DDD32 | +/− | − | | | | |
| DMM45 | + | ++ | | | | |
| DMD01 | + | − | + | ++ | +++/+ | + |

TABLE 11-continued

Summary of functional characterization of HER2 AAV clones

| Clone | Trastuzumab Reactivity Cell lysate | IgG mAb Reactivity | Trastuzumab Reactivity Purified AAV | Avidity Index (5M urea) | rec. HER2 Reactivity (mice sera) | cellular HER2 Reactivity (mice sera) |
|---|---|---|---|---|---|---|
| Consensus 2 | | | | | | |
| DDM53 | + | + | | | | |
| DMD13 | − | − | | | | |
| DMM46 | +/− | + | | | | |
| DMD17 | − | − | | | | |
| DMM38 | + | ++ | | | | |
| DMM41 | − | − | | | | |
| DMM36 | + | + | | | | |
| Consensus 3 | | | | | | |
| DMD09 | − | − | | | | |
| DDM50 | − | − | | | | |
| DMD15 | + | − | + | | +++/+ | ++ |
| DMM43 | + | + | | | | |
| DMM42 | + | + | | | | |
| DDM49 | +/− | + | | | | |
| DMD16 | − | − | | | | |
| Consensus 4 | | | | | | |
| DMM36 | + | + | | | | |
| DMM37 | + | ++ | | | | |
| DDD26 | +/− | − | | | | |
| DMM35 | + | + | | | | |
| DDM48 | + | + | | | | |
| DDD19 | +/− | − | + | +++ | −/+++ | ++ |
| DDDD64 | + | +/− | | | | |
| DMM41 | − | − | | | | |
| Consensus 5 | | | | | | |
| DMD8 | − | − | | | | |
| DMD14 | − | − | | | | |
| DMM34 | − | − | | | | |
| DDD27 | +/− | − | | | | |
| DDD31 | + | +/− | +/− | | | |
| DMM40 | − | − | | | | |
| DMM39 | − | − | | | | |
| DDD24 | + | +/− | | | | |
| DDD30 | + | − | − | ++ | − | − |
| DDD56 | +/− | − | | | | |
| DDD60 | +/− | − | | | | |
| DDD61 | − | − | | | | |
| Consensus 6 | | | | | | |
| DMD10 | − | − | | | | |
| DMM33 | +++ | +++ | | | | |
| DDD58 | +/− | − | | | | |
| DMM43 | + | + | | | | |
| No consensus | | | | | | |
| DMD12 | +/− | − | | | | |
| DDD59 | +/− | − | | | | |

Background and Aims.

Cancer is one of the major public health problems in western societies, leading to every fourth case of death in Austria. Highest prevalence rates are described for breast cancer, affecting currently more than 50 000 women in Austria. To date, passive immunotherapy with monoclonal antibodies is a well-established option in clinical oncology. In contrast, anti-cancer vaccines are less advanced. The development of therapeutic vaccines is still a great challenge mostly due to the self-nature of tumor antigens. Mimotopes, small peptides from 6-38 amino acids, resembling B-cell epitopes do not need consensus sequence with the natural antigen, because molecular mimicry via e g amino acid charges is sufficient to shape an electron cloud specifically recognized by the immune system. As they are similar, but not identical to the original tumor antigen, vaccination with mimotopes may overcome tumor tolerance. Adeno-associated virus like particles (AAVLP) could serve as novel vectors for displaying mimotopes to the immune system. We suggest that cancer vaccines will especially open up new treatment options in minimal residual disease and early stage disease.

Methods and Results:

Adeno-associated viruses (AAV) are ssDNA viruses being replication defective in the absence of Adenovirus. Their surface consists of 60 capsomers, which can be exploited for high density display of recombinant peptides. AAV-like particles (AAVLP) can be generated via assembling recombinant AAV-2 capsid fusion proteins. In this study different HER-2 derived linear B-cell epitopes, generated in a biopanning with the clinically used anti-HER-2 antibody trastuzumab, were inserted into AAV-2. Mimotope candidates were screened for trastuzumab binding in ELISA. Appropriate candidates were employed for immunization of BALB/c mice Immune response was monitored measuring circulating levels of IgG1, IgG2a and IgG2b antibodies reactive to recombinant HER-2. Molecular mimicry was also proved in immunofluorescence on human HER-2 overexpressing murine mammary carcinoma D2F2-E2 cells. Sera of mice displaying highest HER-2 specific antibody levels were exploited for antibody purification and purified antibodies were tested for their tumoristatic properties in a tetrazolium based cell viability assay. In this assay HER-2 overexpressing human mammary carcinoma cells mBT474 showed significant growth reduction even after 24 h of antibody incubation with purified antibodies of clone DMD1. This effect increased at consecutive measurements after 48 and 72 h.

Conclusion:

In this study we could demonstrate that AAVLP are suitable vectors for mimotope based cancer vaccines. In our system immunized BALBc mice developed anti-HER-2 antibodies with similar biological properties to the clinically used monoclonal antibody trastuzumab. Due to their easy application and economic advantages, cancer vaccines might become important supplementary therapy options in cancer treatment, especially in the minimal residual disease setting.

9. Memory Effect

A further experiment was carried out to investigate the memory effect elicited by one species of AAV particles comprising a mimotope insert in combination with different adjuvants. 8 mice per groups were immunized subcutaneously according to Table 12 three times with two weeks intervals. For sera samples, blood was collected before starting of the first immunisation (pre-immunsera; PIS), and at days 13 (1. MIS), 27 (2. MIS), 41 (3. MIS), 69 (4. MIS), 97 (5. MIS), 125 (6. MIS) and at sacrifice of mice (7. MIS).

TABLE 122

Immunization scene

| Group | Adjuvant | Antigen |
|-------|----------|---------|
| A | Alum | 10 µg DMD2 |
| B | MPL | 10 µg DMD2 |
| C | Alum + MPL | 10 µg DMD2 |
| D | ODN-1826 | 10 µg DMD2 |
| E | Alum + ODN-1826 | 10 µg DMD2 |
| F | Alum | HER-2 |
| G | Naiv | (Iodixanol) |

Figure 8B:
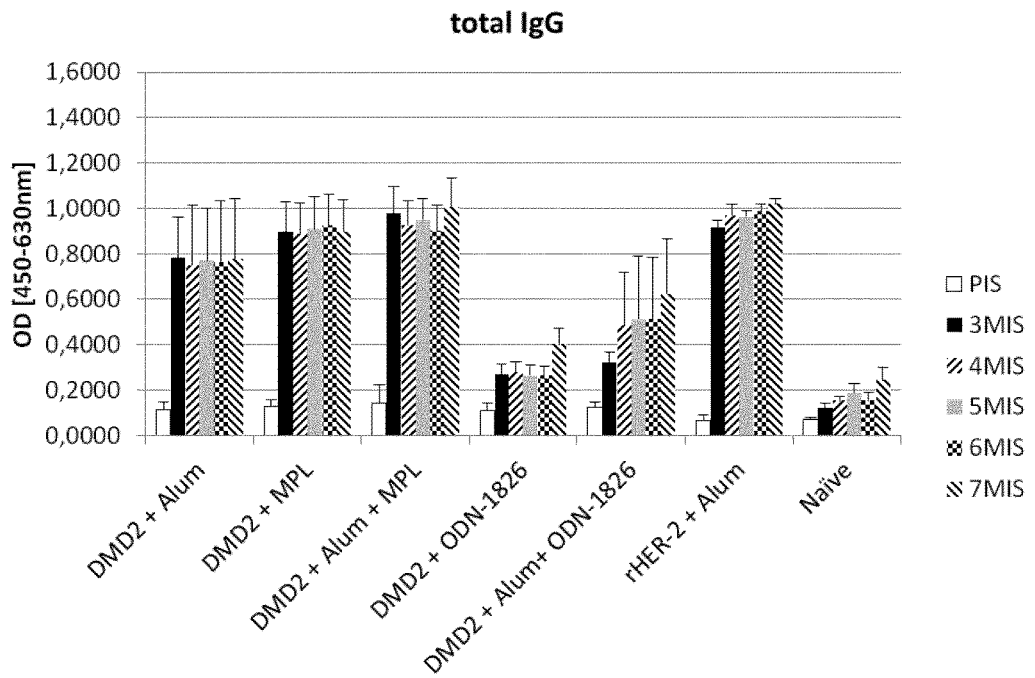

In a first analysis, HER-2 specific total IgG levels of PIS, 1. MIS, 2. MIS and 3. MIS were determined by ELISA as described above. The results are shown in FIG. 8a). To evaluate a potential memory effect a further analysis samples PIS, 3. MIS, 4. MIS, 5. MIS, 6. MIS and 7. MIS were analyzed accordingly. The results are shown in FIG. 8b).

The data show, that AAV particles comprising a HER2 minotope, especially DMD2, were able to induce a long lasting B-cell memory. The highest effect was achieved with a combination of Alum and MPL as adjuvants.

10. Immunofluorescense Staining

D2F2 (control) and D2F2-E2 (transfected with human HER-2) were seeded for a concentration of 2×1 cells in 400 pL per well on four-well immunofluorescence chamber slides (Permanox®, Thernio Scientific). After 24 hours they were fixed with 4% paraformaldehyde for 8 minutes at room temperature before they were washed three times with cold PBS. For DAPI staining, cells were permeabilized 5 minutes with 0.5% TritonX-100 in PBS and washed again with cold PBS. DMD001 sera (as obtained in experiment 8) were diluted 1:20 in PBS/0.5% BSA with 200 pL each well, whereas trastuzumab was incubated with 1 pg/ml each. After an incubation of one hour at room temperature, wells were washed four times with cold PBS, before the secondary antibody, diluted 1:200 in PBS/0.5% BSA was added in 400 pl per well. Incubation was performed by covering slides with aluminum foil for 45 minutes, and stopped by washing slides four times with cold PBS. DAPI diluted 1:5000 was incubated for eight minutes at room temperature and then washed three times with cold PBS. Afterwards all slides were washed in distilled aqua before they were covered with mounting medium (Fluoromount™, Sigma) and stored at 4° C.

Immunofluorescense staining of DMD001 sera on D2F2-E2 cells (a), of DMD001 sera on D2F2 cells (b) and trastuzumab on D2F2-E2 cells (c) showed green fluoresce labeling of cells for conditions (a) and (c) but not for (b), indicative for the presence of HER-2 specific in DMD001 sera in comparison to the positive control with trastuzumab (data not shown).

REFERENCES

Bernhard, H., et al. (2002). "Vaccination against the HER-2/neu oncogenic protein." *Endocr Relat Cancer* 9(1): 33-44.

Büning, H., et al. (2008) "Mutated Parvovirus Structural Proteins as Vaccines." PCT/EP2008/004366, MediGene AG, Ludwig-Maximilians-Universität, Klinikum der Universität zu Köln.

Corpet, F. (1988). "Multiple sequence alignment with hierarchical clustering." *Nucleic Acids Res* 16(22): 10881-90.

Dakappagari, N. K., et al. (2000). "Prevention of mammary tumors with a chimeric HER-2 B-cell epitope peptide vaccine." *Cancer Res* 60(14): 3782-9.

Dakappagari, N. K., et al. (2005). "Conformational HER-2/neu B-cell epitope peptide vaccine designed to incorporate two native disulfide bonds enhances tumor cell binding and antitumor activities." *J Biol Chem* 280(1): 54-63.

Dakappagari, N. K., et al. (2003). "A chimeric multi-human epidermal growth factor receptor-2 B cell epitope peptide vaccine mediates superior antitumor responses." *J Immunol* 170(8): 4242-53.

Disis, M. L., et al. (2002). "Generation of T-cell immunity to the HER-2/neu protein after active immunization with HER-2/neu peptide-based vaccines." *J Clin Oncol* 20(11): 2624-32.

Disis, M. L., et al. (1999). "Generation of immunity to the HER-2/neu oncogenic protein in patients with breast and ovarian cancer using a peptide-based vaccine." *Clin Cancer Res* 5(6): 1289-97.

Disis, M. L., et al. (1996). "Peptide-based, but not whole protein, vaccines elicit immunity to HER-2/neu, oncogenic self-protein." *J Immunol* 156(9): 3151-8.

Disis, M. L., et al. (2009). "Concurrent trastuzumab and HER2/neu-specific vaccination in patients with metastatic breast cancer." *J Clin Oncol* 27(28): 4685-92.

Ercolini, A. M., et al. (2003). "Identification and characterization of the immunodominant rat HER-2/neu MHC class I epitope presented by spontaneous mammary tumors from HER-2/neu-transgenic mice." *J Immunol* 170(8): 4273-80.

Esserman, L. J., et al. (1999). "Vaccination with the extracellular domain of p185neu prevents mammary tumor development in neu transgenic mice." *Cancer Immunol Immunother* 47(6): 337-42.

Friedlander, E., et al. (2008). "ErbB-directed immunotherapy: antibodies in current practice and promising new agents." *Immunol Lett* 116(2): 126-40.

Grimm, D., et al. (1999). "Titration of AAV-2 particles via a novel capsid ELISA: packaging of genomes can limit production of recombinant AAV-2." *Gene Ther* 6(7): 1322-30.

Harries, M. and I. Smith (2002). "The development and clinical use of trastuzumab (Herceptin)." *Endocr Relat Cancer* 9(2): 75-85.

Heilbronn, R., et al. (1990). "The adeno-associated virus rep gene suppresses herpes simplex virus-induced DNA amplification." *J Virol* 64(6): 3012-8.

Hörer, M. and M. Hallek (2005) "Method of producing a recombinant adeno-associated virus, suitable means for producing the same and use thereof for producing a medicament." U.S. Ser. No. 09/913,240, MediGene AG.

Hynes, N. E., et al. (1994). "The biology of erbB-2/neu/HER-2 and its role in cancer Targeting HER2 in other tumor types." *Biochim Biophys Acta* 1198(2-3): 165-84.

Jasinska, J., et al. (2003). "Inhibition of tumor cell growth by antibodies induced after vaccination with peptides derived from the extracellular domain of Her-2/neu." *Int J Cancer* 107(6): 976-83.

Ladjemi, M. Z., et al. (2010). "Anti-HER2 vaccines: new prospects for breast cancer therapy." *Cancer Immunol Immunother* 59(9): 1295-312.

Müller, V., et al. (2009). "Immunological Approaches in the Treatment of Metastasized Breast Cancer." *Breast Care (Basel)* 4(6): 359-366.

Nahta, R. and F. J. Esteva (2006). "Herceptin: mechanisms of action and resistance." *Cancer Lett* 232(2): 123-38.

Partidos, C. D. (2000). "Peptide mimotopes as candidate vaccines." *Curr Opin Mol Ther* 2(1): 74-9.

Peoples, G. E., et al. (2008). "Combined clinical trial results of a HER2/neu (E75) vaccine for the prevention of recurrence in high-risk breast cancer patients: U.S. Military Cancer Institute Clinical Trials Group Study I-01 and I-02." *Clin Cancer Res* 14(3): 797-803.

Perabo, L., et al. (2003) "A library of modified structural genes or capsids modified particles useful for the identification of viral clones with desired cell tropism." PCT/EP2002/014750, MediGene AG.

Reilly, R. T., et al. (2000). "HER-2/neu is a tumor rejection target in tolerized HER-2/neu transgenic mice." *Cancer Res* 60(13): 3569-76.

Riemer, A. B. and E. Jensen-Jarolim (2007). "Mimotope vaccines: epitope mimics induce anti-cancer antibodies." *Immunol Lett* 113(1): 1-5.

Riemer, A. B., et al. (2004). "Generation of Peptide mimics of the epitope recognized by trastuzumab on the oncogenic protein Her-2/neu." *J Immunol* 173(1): 394-401.

Ross, J. S., et al. (2009). "The HER-2 receptor and breast cancer: ten years of targeted anti-HER-2 therapy and personalized medicine." *Oncologist* 14(4): 320-68.

Scholl, S., et al. (2001). "Targeting HER2 in other tumor types." *Ann Oncol* 12 Suppl 1(1): S81-7.

Slamon, D. J., et al. (2001). "Use of chemotherapy plus a monoclonal antibody against HER2 for metastatic breast cancer that overexpresses HER2." *N Engl J Med* 344(11): 783-92.

Sonntag, F., et al. (2010a) "Assembly activating protein (AAP) and its use for the manufacture of parvovirus particles essentially consisting of VP3." PCT/EP2010/001343, Deutsches Krebsforschungszentrum, MediGene AG.

SONNTAG, F., et al. (2010b) A viral assembly factor prornotes AAV2 capsid formation in the nucleolus. *Proc Natl Acad Sci USA*, 107, 10220-5.

Vogel, C. L., et al. (2002). "Efficacy and safety of trastuzumab as a single agent in first-line treatment of HER2-overexpressing metastatic breast cancer." *J Clin Oncol* 20(3): 719-26.

Warrington, K. H., Jr., et al. (2004). "Adeno-associated virus type 2 VP2 capsid protein is nonessential and can tolerate large peptide insertions at its N terminus." *J Virol* 78(12): 6595-609.

The invention claimed is:

1. Parvovirus mutated structural protein for inducing a B-cell response against human epidermal growth factor receptor (HER2), which comprises one or more mimotopes of HER2 capable of specifically binding to an antibody directed against HER2, wherein at least one of the mimotopes comprises an amino acid sequence of SEQ ID NO: 66, SEQ ID NO: 70, SEQ ID NO: 71, SEQ ID NO: 72, SEQ ID NO: 73, SEQ ID NO: 74, SEQ ID NO: 76, SEQ ID NO: 77, SEQ ID NO 79, SEQ ID NO: 80, SEQ ID NO: 81, SEQ ID NO: 83, SEQ ID NO: 84, SEQ ID NO: 85, SEQ ID NO: 87, SEQ ID NO: 88, SEQ ID NO: 89, SEQ ID NO: 91, SEQ ID NO: 92, SEQ ID NO: 93, SEQ ID NO: 94, SEQ ID NO: 95, SEQ ID NO: 97, SEQ ID NO: 98 or SEQ ID NO: 99.

2. Parvovirus mutated structural protein according to claim 1, wherein the antibody is Trastuzumab or Pertuzumab.

3. Parvovirus mutated structural protein according to claim 1, wherein a plurality of structural proteins is capable of forming a capsomeric structure, capsid or virus-like particle.

4. Parvovirus mutated structural protein according to claim 3, wherein the one or more mimotopes of HER2 are arranged in the parvovirus mutated structural protein to be located on the surface of the capsomeric structure, capsid or virus-like particle.

5. Parvovirus mutated structural protein according to claim 1, wherein the parvovirus is selected from the group consisting of adeno-associated virus (AAV), bovine AAV (b-AAV), canine AAV (CAAV), canine parvovirus (CPV), mouse parvovirus, minute virus of mice (MVM), B19, H1, avian AAV (AAAV), feline panleukopenia virus (FPV), and goose parvovirus (GPV).

6. Parvovirus mutated structural protein according to claim 5, wherein the AAV is AAV-1, AAV-2, AAV-3b, AAV-4, AAV-5, AAV-6, AAV-7, AAV-8, AAV-9, AAV-10, AAV-11, or AAV-12.

7. Parvovirus mutated structural protein according to claim 1, wherein the parvovirus mutated structural protein is a fusion protein further comprising a second protein or peptide domain.

8. Parvovirus mutated structural protein according to claim 1, wherein at least one of the mimotopes is not present in a wild type parvoviral structural protein, or wherein the wild type parvoviral structural protein is not capable of specifically binding to Trastuzumab.

9. A multimeric structure comprising parvovirus mutated structural proteins according to claim 1, wherein the structure is an aggregate of at least 5, at least 10, at least 30, or at least 60 mutated structural proteins.

10. The multimeric structure according to claim 9, wherein the multimeric structure is a capsomeric structure, capsomer, a capsid, a virus-like particle, or a virus.

11. The multimeric structure according to claim 9, wherein the one or more HER2 mimotopes are located on the surface of the multimeric structure.

12. The multimeric structure according to claim 9, wherein the spacing of at least two HER2 mimotopes on the surface of one multimeric structure is 10-500 angstroms, 50-300 angstroms, or 80 to 120 angstroms.

13. A medicament for treating or preventing a HER2-related disease, the medicament comprising at least one parvovirus mutated structural protein according to claim 1, and at least one suitable excipient, carrier, and/or stabilizer.

14. A vaccine comprising at least one parvovirus mutated structural protein according to claim 1, and at least one suitable adjuvant, excipient, carrier, and/or stabilizer.

15. The vaccine according to claim 14, wherein the adjuvant is selected from the group consisting of mineral oil-based adjuvants, oil in water emulsion adjuvants, syntax adjuvant formulation containing muramyl dipeptide, and aluminum salt adjuvants.

16. The vaccine according to claim 15, wherein the adjuvant is selected from the group consisting of Freund's complete or incomplete adjuvant, CpG, imidazoquinoline, MPL, MDP, MALP, flagellin, LPS, LTA, cholera toxin, a cholera toxin derivative, HSP60, HSP70, HSP90, saponins, QS21, ISCOMs, CFA, SAF, MF59, admamantane, aluminum hydroxide, aluminum phosphate, and a cytokine.

17. The vaccine according to claim 14, wherein the vaccine comprises a combination of more than one, adjuvants.

18. A medicament comprising at least one parvovirus mutated structural protein according to claim 1, and at least one suitable excipient, carrier, and/or stabilizer.

19. A method of inducing a B-cell response against HER2, the method comprising administering the Parvovirus mutated structural protein according to claim 1, in an effective dose to a mammal.

20. The method of inducing a B-cell response according to claim 19, wherein the parvovirus mutated structural protein is administered parenterally.

21. The method according to claim 19, wherein the Parvovirus mutated structural protein is administered multiple times.

22. A method of treating a HER2-related disease, the method comprising administering the Parvovirus mutated structural protein according to claim 1, in an effective dose to a mammal.

23. The method according to claim 22, wherein the HER2-related disease is cancer.

24. A nucleic acid coding for a parvovirus mutated structural protein according to claim 1.

25. An expression cassette, construct, or vector comprising the nucleic acid according to claim 24.

26. A cell comprising the expression cassette, construct, or vector according to claim 24.

27. The cell according to claim 26, wherein the cell is a bacterium, a yeast cell, an insect cell, or a mammalian cell.

28. A method of preparing a structural protein, the method comprising:
   a) expressing a nucleic acid coding for a parvovirus mutated structural protein by cultivating a the cell according to claim 26 under suitable conditions, and
   b) isolating the expressed parvovirus mutated structural protein of step a).

29. A composition for inducing a B-cell response comprising:
   a) a support capable of presenting peptides in a repetitive array; and
   b) at least three peptides, identical and/or different, each having an amino acid sequence independently selected from SEQ ID NO: 70, SEQ ID NO: 71, SEQ ID NO: 72, SEQ ID NO: 73, SEQ ID NO: 74, SEQ ID NO: 76, SEQ ID NO: 77, SEQ ID NO: 80, SEQ ID NO: 81, SEQ ID NO: 84, SEQ ID NO: 85, SEQ ID NO: 87, SEQ ID NO: 88, SEQ ID NO: 89, SEQ ID NO: 91, SEQ ID NO: 92, SEQ ID NO: 93, SEQ ID NO: 94, SEQ ID NO: 95, SEQ ID NO: 97, SEQ ID NO: 98, or SEQ ID NO: 99, the peptides being joined to the support so as to form a HER2 mimotope-presenting support.

30. The composition according to claim 29, wherein the support is selected from the group consisting of a bead, a lipid membrane, a protein, or an inorganic carrier.

31. The composition according to claim 30, wherein the bead is selected from a polyacrylamide bead, an agarose bead, a polystyrene bead, a magnetic bead, a latex particle, a carbohydrate assembly.

32. The composition according to claim 30, wherein the lipid membrane is selected from a lipid assembly and a liposome.

33. The composition according to claim 30, wherein the protein is a protein assembly comprising a structural protein of a virus or phage, a virus-like particle or a virus; a polymer; KLH (Keyhole limpet hemocyanin); or LPH (Hemocyanin from Limulus *polyphemus* hemolymph).

34. The composition according to claim 30, wherein the inorganic carrier is selected from silica material and wherein the one or more HER2 mimotopes are covalently linked through a hydroxy, carboxy, or amino group and with a reactive group on the carrier.

35. Parvovirus mutated structural protein for inducing a B-cell response against human epidermal growth factor receptor (HER2) which comprises one or more mimotopes of HER2 capable of specifically binding to an antibody directed against HER2, wherein at least one of the mimotopes comprises an amino acid sequence of any one of SEQ ID NO: 100-166 or a sequence thereof having one or two amino acid substitutions.

* * * * *